United States Patent
Pi

(10) Patent No.: US 8,673,650 B2
(45) Date of Patent: Mar. 18, 2014

(54) OPTICAL MOLECULAR DETECTION

(75) Inventor: Bo Pi, Carlsbad, CA (US)

(73) Assignee: Ridge Diagnostics, Inc., La Jolla, CA (US)

( * ) Notice: Subject to any disclaimer, the term of this patent is extended or adjusted under 35 U.S.C. 154(b) by 610 days.

(21) Appl. No.: 12/305,950

(22) PCT Filed: Dec. 11, 2006

(86) PCT No.: PCT/US2006/047244
§ 371 (c)(1),
(2), (4) Date: May 21, 2009

(87) PCT Pub. No.: WO2007/067819
PCT Pub. Date: Jun. 14, 2007

(65) Prior Publication Data
US 2010/0144052 A1  Jun. 10, 2010

Related U.S. Application Data

(60) Provisional application No. 60/748,824, filed on Dec. 9, 2005, provisional application No. 60/784,322, filed on Mar. 21, 2006, provisional application No. 60/796,585, filed on May 1, 2006.

(51) Int. Cl.
*G01N 21/00* (2006.01)
(52) U.S. Cl.
USPC ........... 436/164; 436/172; 436/805; 356/364; 356/369; 435/6.1; 435/287.2; 435/288.7
(58) Field of Classification Search
None
See application file for complete search history.

(56) References Cited

U.S. PATENT DOCUMENTS

| 6,060,237 | A | 5/2000 | Nygren et al. |
|---|---|---|---|
| 6,159,681 | A | 12/2000 | Zebala |
| 6,738,141 | B1 | 5/2004 | Thirstrup |
| 6,882,420 | B2 | 4/2005 | Rassman et al. |
| 2002/0088919 | A1 | 7/2002 | Muramatsu |
| 2004/0151629 | A1 | 8/2004 | Pease et al. |

OTHER PUBLICATIONS

Suzuki, M., et al. Standardized procedure for calibrating height scales in atomic force microscopy on the order of 1 nm, 1996, Journal of vaccum science and technology, A. vol. 14(3), p. 1228-1232.*
Polder, G., et al., "Calibration and Characterization of Spectral Imaging Systems," *SPIE Proceedings—Multispectral and Hyperspectral Image Acquisition and Processing*, vol. 4548, pp. 10-17, (2001).
International Search Report and Written Opinion dated Mar. 13, 2008 for International Application No. PCT/US2006/047244, filed Dec. 11, 2006 (13 pages).
International Preliminary Report on Patentability dated Mar. 12, 2009 for International Application No. PCT/US2006/047244, filed Dec. 11, 2006 (12 pages).

* cited by examiner

*Primary Examiner* — Robert Xu
(74) *Attorney, Agent, or Firm* — Fish & Richardson P.C.

(57) ABSTRACT

Optical detection of molecules using a biochip having at least one reagent immobilizing area designed to receive one or more reagents and at least one calibration structure with a predetermined height to provide a height reference for optical measurement is disclosed. When the calibration structure is illuminated by a probe beam of light, a first reflected beam of light is reflected off the calibration structure, and a second reflected beam of light is reflected off the reagent immobilizing area. The first reflected beam and the second reflected beam are compared to determine a height at the reagent immobilizing area.

21 Claims, 16 Drawing Sheets

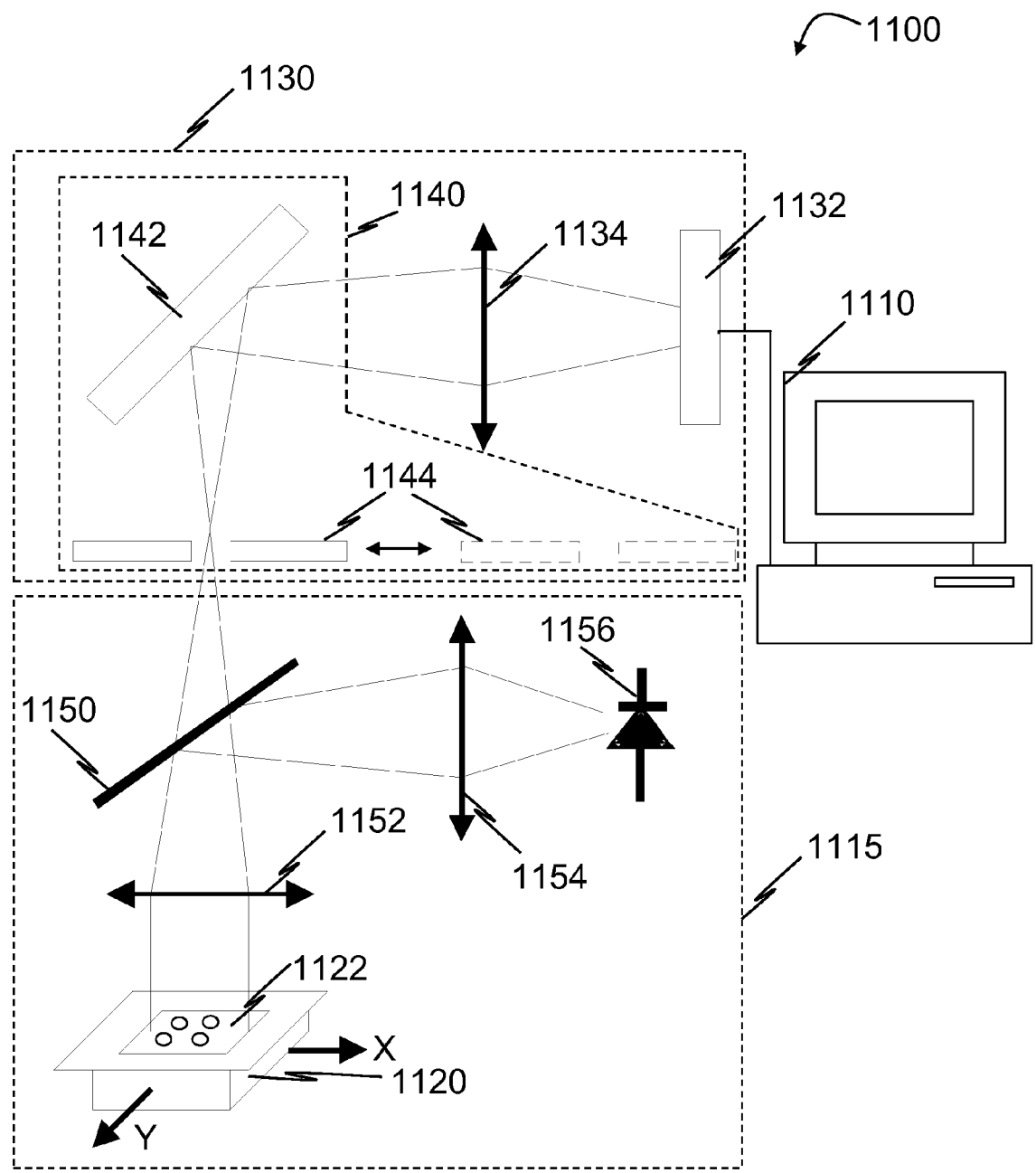
11A

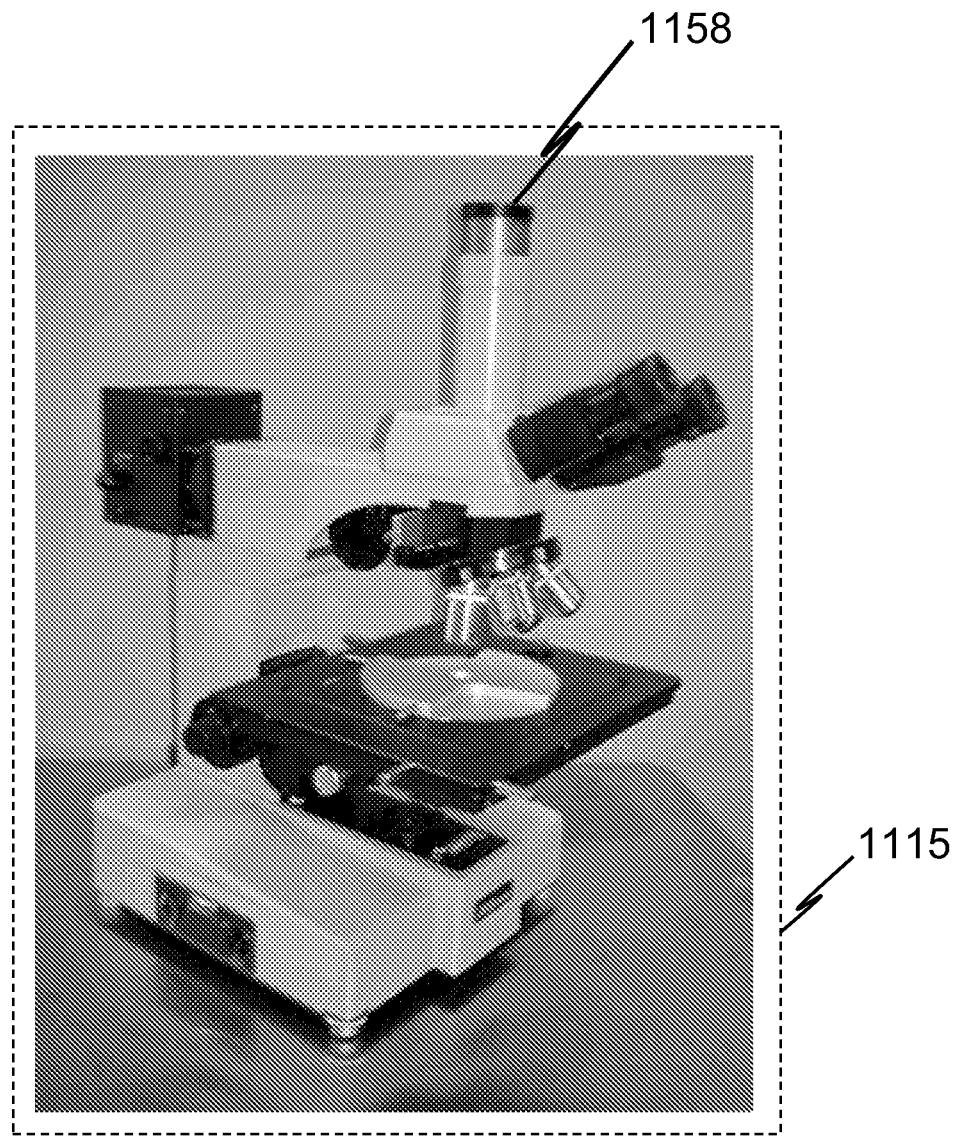
11B

OPTICAL MOLECULAR DETECTION

This application is a National Stage application under 35 U.S.C. §371 and claims benefit under 35 U.S.C. §119(a) of International Application No. PCT/US06/47244 having an International Filing Date of Dec. 11, 2006, which, in turn, claims the benefits of the filing dates of U.S. patent application Ser. No. 60/748,824, filed on Dec. 9, 2005 and entitled "Molecule Interaction Measurement Chip and System;" U.S. patent application Ser. No. 60/784,322, filed on Mar. 21, 2006 and entitled "Molecular Interaction Detection Chip and Fabrication Process;" and U.S. patent application Ser. No. 60/796,585, filed on May 1, 2006 and entitled "Precision Molecule Interaction Measurement System and Method." The contents of U.S. patent application Ser. No. 60/748,824, U.S. patent application Ser. No. 60/784,322, and U.S. patent application Ser. No. 60/796,585 are incorporated by reference as part of this application.

TECHNICAL FIELD

This application relates to detecting molecules and molecular interactions.

BACKGROUND

Various assays, such as immunoassay uses reagents to determine a presence of particular molecules or molecule clusters, including, e.g., biomolecules such as protein. In applications, antibodies have been used as reagents to detect molecular interactions with specific antigens. Some assays, such as Enzyme-Linked ImmunoSorbent Assay (ELISA) are easy to implement but are limited to quantitative analysis.

SUMMARY

Techniques for detecting and measuring molecular interactions are disclosed.

In one aspect, an apparatus for detecting molecular interactions includes a substrate and a target layer deposited on the substrate. The target layer contains a reagent immobilizing area designed to receive one or more reagents and a calibration structure having a predetermined height. When illuminated by a probe beam of light, a first reflected beam of light reflected off the calibration structure is compared to a second reflected beam of light reflected off the reagent immobilizing area to determine a height at the reagent immobilizing area.

Implementations can optionally include one or more of the following features. The predetermined height of the calibration structure can be less than the coherent length of the probe beam of light. The apparatus can include a cartridge having a support structure for receiving the substrate. Also, a memory device can be disposed on the cartridge with the memory device designed to store data related to the substrate. Alternatively, a memory device can be disposed directly on the substrate. In addition, the substrate can include a transparent layer that at least partially transmits light. The optional transparent layer can be deposited just below the transparent layer. The target layer can be composed of a material having an index of refraction different than the transparent layer. In some implementations, a reflective layer is disposed between the transparent layer and the target layer. The reflective layer has an index of refraction different than the target layer and the transparent layer, and the reflective layer is designed to at least partially reflect light.

Further, implementations can optionally include one or more of the following features. The target layer can be composed of a polymer coating. An optional polymer layer can be deposited on the calibration structure with the polymer layer Designed to resist absorption of the reagents. In addition, the calibration structure can include a positive structure having a predetermined height greater than the height at the reagent immobilizing area. The calibration structure can also include a negative structure having a predetermined height less than the height at the reagent immobilizing area. In addition, a physical barrier can be deposited on the target layer with the physical barrier having a barrier height greater than the height at the reagent immobilizing area to prevent movement of reagents beyond the barrier. Alternatively, a reference structure can be deposited on the target layer of the substrate with the reference structure having a reference height greater than a coherent length of a source light. This reference structure can prevent any further deposition of molecules to the area of surface of the target layer located under the reference structure. When a source probe beam of light is directed at the reference structure, a reflected beam of light reflected off the reference structure does not interfere with a reflected beam of light reflected off the target layer. Further, a plurality of alignment markers of a predetermined shape can be deposited on the substrate. The alignment markers are deposited at predetermined locations relative to the reagent immobilizing area on the substrate. Also, a cover can be removably deposited on the cartridge, with the cover designed to protect the substrate.

In another aspect, an imaging system for detecting molecular interaction includes a light probe. The light probe further includes a light source designed to direct a probe beam of light along an optical light path, one or more optical lenses located along the light path, and an optical grating located along the light path. The optical grating is designed to switch between a zero optical mode and a first optical mode. The optical probe also includes an optical slit designed to switch between a position on the light path and a position off the light path. The imaging system also includes a substrate with a target layer deposited on the substrate. The target layer has a reagent immobilizing area designed to receive one or more reagents. A sample stage is also included with the imaging system with the sample stage designed to hold and move the substrate along a predetermined plane perpendicular to the light path. The imaging system further includes an image sensor located along the light path with the image sensor designed to capture the probe beam of light reflected off the substrate.

Implementations can optionally include one or more of the following features. The imaging system can include an imaging mode controller designed to switch the optical grating between the zero optical mode and the first optical mode. The imaging mode controller can also move the optical slit between the position on the light path and the position off the light path. In some implementations, the imaging mode controller can also switch the optical grating to the first optical mode and move the optical slit on the light path in such a manner as to direct a single line of the reflected beam of light is through the optical slit and the optical grating to disperse the single line of the reflected beam of light into spectral components.

In addition, implementations can optionally include one or more of the following features. The imaging system can include one or more additional optical slits and optical gratings. Also, the imaging mode controller can be designed to switch the optical gratings to the first optical mode and move the optical slits on the light path in such a manner as to direct a different line of the reflected beam of light through each of the optical slits and the optical gratings to disperse each line of the reflected beam of light into spectral components. Image sensor can be designed to determine the height at the reagent immobilizing area based on the spectral components of the reflected beam of light. The light source can be designed to direct a probe beam of light having a coherent length based on a height of the substrate. Further the image sensor can include a charge coupled device (CCD) image sensor. Alternatively, the image sensor can include a complementary metal oxide semiconductor (CMOS) image sensor.

In yet another aspect, molecular interactions are detected by providing a biochip. The biochip includes a substrate and a target layer deposited on the substrate with the target layer having a reagent immobilizing area designed to receive one or more reagents. The biochip also includes a calibration structure with a predetermined height deposited on the substrate. Molecular interaction is detected by depositing reagent molecules on the reagent immobilizing area to promote absorption of the reagent molecules on a surface of the reagent immobilizing area. Also, target molecules are deposited on the reagent immobilizing area to promote molecular interactions between the immobilized reagent molecules and the target molecules. Images of the biochip is captured to detect a level of molecular interaction between the immobilized reagent molecules and the target molecules.

Implementations can optionally include one or more of the following features. Capturing the images of the biochip can include illuminating the biochip with a probe beam of light, and capturing a plurality of reflected beams of light reflected off a plurality of locations on the biochip including a first reflected beam of light reflected off the calibration structure, a second reflected beam of light reflected off the reagent immobilizing area and a third reflected beam of light reflected off a clean area. The captured reflected beams of light can be analyzed to detect molecular interactions between the reagents and the target molecules. Also, analyzing the captured reflected beams of light can include obtaining spectral data of the captured reflected beams of light. Based on the spectral data obtained, various height measurements can be determined. The height measurements obtained correspond to the locations of light reflection on the biochip including a calibration structure height, a reagent immobilizing area height and a clean area height.

Implementations can further optionally include one or more of the following features. Capturing the images can include capturing a first image before depositing the target molecules and a second image after depositing the target molecules. The first and second images can be further analyzed. The first and second images can be normalized by subtracting the clean area height from the calibration structure height and the reagent immobilizing area height. Also, a scaling factor can be calculated by determining a percent change in the normalized calibration structure height between the first and second images. Further, the molecular interaction between the target molecules and the immobilized reagent molecules can be detected by calculating an increase in the reagent immobilizing area height between the first and second images and multiplying the increase by the scaling factor. When depositing the target molecules, biomarker molecules of interest can also be deposited and, detecting a level of molecular interaction can include detecting molecular interactions between the immobilized reagent molecules and the biomarker molecules Implementations can also optional include one or more of the following features. Depositing the reagent molecules can include depositing reagent molecules labeled with one or more florescent dye labels. Also, capturing images of the biochip can include capturing a first image before depositing the target molecules and a second image after depositing the target molecules. A level of molecular interaction between the immobilized reagent molecules and the target molecules can be detected by determining a level of emission produced by the florescent dye labels in response to the interactions between the labeled reagent molecules and the target molecules.

In another aspect, molecular interactions are detected by providing at least one reagent immobilizing area over a substrate designed to receive at least one reagent which combines with a target molecule. Also, at least one calibration structure is provided at a location displaced from the regent immobilizing area to have a predetermined height different from a surface of the reagent immobilizing area to provide a height reference for optical measurement. In addition, a probe beam is illuminated to the reagent immobilizing area and the calibration structure to obtain a first optical signal from the reagent immobilizing area which includes height information of the reagent immobilizing area and a second optical signal from the calibration structure which include height information of the calibration structure. The first and the second optical signals are compared to determine a height at the reagent immobilizing area based on the predetermined height of the calibration structure.

Implementations can optionally include one or more of the following features. The probe beam can be scanned across the substrate to illuminate other reagent immobilizing areas and calibration structures to obtain optical measurements of the other reagent immobilizing areas.

In another aspect, an apparatus includes a biochip for detecting molecular interactions, the biochip includes a substrate. The substrate includes a target layer having at least one reagent immobilizing area designed to receive one or more reagents. The substrate also includes a memory device disposed on the substrate, the memory device designed to store data related to the substrate.

In another aspect, an apparatus includes a biochip for detecting molecular interactions. The biochip includes a substrate with a target layer having at least one reagent immobilizing area designed to receive one or more reagents. The biochip also includes a cartridge having a support structure for receiving the substrate. A memory device is disposed on the cartridge with the memory device designed to store data related to the substrate.

In another aspect, an apparatus for detecting molecular interactions includes a biochip. The biochip includes a substrate having a sample surface and at least one reagent immobilizing area on the sample surface designed to receive at least one immobilizing reagent that interacts and immobilizes target molecules. The biochip also includes at least one calibration feature formed on the substrate adjacent to the reagent immobilizing area and having a calibration surface above or below the sample surface by a distance that is less than a coherent length of a probe light beam that is used to illuminate the biochip and to optically measure presence of the target molecules immobilized at the reagent immobilizing area.

Implementations can optionally include one or more of the following features. The biochip can also include a cartridge having a support structure for housing the substrate. Also, a memory device can be deposited on the cartridge with the memory device designed to store data related to the biochip. Alternatively, a memory device can be deposited on the substrate. The substrate can further include a transparent layer that at least partially transmits light with the transparent layer deposited below the sample surface. The substrate can also include a reflective layer disposed between the transparent layer and the sample surface with the reflective layer having an index of refraction different than the sample layer and the transparent layer and designed to at least partially reflect light.

Implementations can also optionally include one or more of the following features. The calibration structure can include a positive structure having a predetermined height greater than the surface of the reagent immobilizing area. The calibration structure can also include a negative structure having a predetermined height less than the surface of the reagent immobilizing area. The biochip can also include a physical barrier disposed on the sample surface, the physical barrier having a barrier height greater than the surface of the reagent immobilizing area. The biochip can further include a reference structure disposed on the sample surface of the substrate, the reference structure having a height greater than a coherent length of a source light, wherein the source light directed at the reference structure is reflected off the reference structure but does not interfere with a light beam that is reflected off the sample surface.

In another aspect, an imaging system for detecting molecular interaction includes a light probe. The light probe further includes a light source designed to direct a probe beam of light along an optical light path, one or more optical lenses located along the light path, and an optical grating located along the light path. The optical grating is designed with a first optical mode. The optical probe also includes an optical slit deposited on the light path. The imaging system also includes a substrate with a target layer deposited on the substrate. The target layer has a reagent immobilizing area designed to receive one or more reagents. A sample stage is also included with the imaging system with the sample stage designed to hold and move the substrate along a predetermined plane perpendicular to the light path. The imaging system further includes an image sensor located along the light path with the image sensor designed to capture the probe beam of light reflected off the substrate.

Implementations can optionally include one or more of the following features. The imaging system can include an optical grating designed to switch between a zero optical mode and a first optical mode. The optical probe can also include an optical slit designed to switch between a position on the light path and a position off the light path. The imaging system can further include an imaging mode controller designed to switch the optical grating between the zero optical mode and the first optical mode. The imaging mode controller can also move the optical slit between the position on the light path and the position off the light path. In some implementations, the imaging mode controller can also switch the optical grating to the first optical mode and move the optical slit on the light path in such a manner as to direct a single line of the reflected beam of light is through the optical slit and the optical grating to disperse the single line of the reflected beam of light into spectral components.

In yet another aspect, molecular interactions are detected by providing a biochip. The biochip includes a substrate and a target layer deposited on the substrate with the target layer having a reagent immobilizing area designed to receive one or more reagents. Molecular interaction is detected by depositing reagent molecules on the reagent immobilizing area to promote absorption of the reagent molecules on a surface of the reagent immobilizing area. Also, target molecules are deposited on the reagent immobilizing area to promote molecular interactions between the immobilized reagent molecules and the target molecules. Images of the biochip is captured to detect a level of molecular interaction between the immobilized reagent molecules and the target molecules.

Implementations can optionally include one or more of the following features. The biochip can also include a calibration structure with a predetermined height deposited on the substrate. Capturing the images of the biochip can include illuminating the biochip with a probe beam of light, and capturing a plurality of reflected beams of light reflected off a plurality of locations on the biochip including a first reflected beam of light reflected off the calibration structure, a second reflected beam of light reflected off the reagent immobilizing area and a third reflected beam of light reflected off a clean area. The captured reflected beams of light can be analyzed to detect molecular interactions between the reagents and the target molecules. Also, analyzing the captured reflected beams of light can include obtaining spectral data of the captured reflected beams of light. Based on the spectral data obtained, various height measurements can be determined. The height measurements obtained correspond to the locations of light reflection on the biochip including a calibration structure height, a reagent immobilizing area height and a clean area height.

The subject matter described in this specification can be implemented as a method or as a system.

DESCRIPTION OF DRAWINGS

FIGS. 1B, 1C, 10, 1E, 1F and 1G are cross sectional views of a biochip detailing various components.

FIGS. 11A and 11B are functional block diagrams of a hyperspectrum imaging system designed to function with an existing microscopic system.

Like reference symbols in the various drawings indicate like elements.

DETAILED DESCRIPTION

Examples of optical techniques for detecting and measuring molecules and molecular interactions using biochips are disclosed. Biochips described in this application can be used to provide a platform to support at least one sample such as a liquid sample and to expose the liquid sample to optical probe light for optical detection. A suitable liquid sample may be in various forms, e.g., a solution that contains a sample material, or a blood sample or other body fluid sample from a patient.

Biochip Design

Figure 1A:
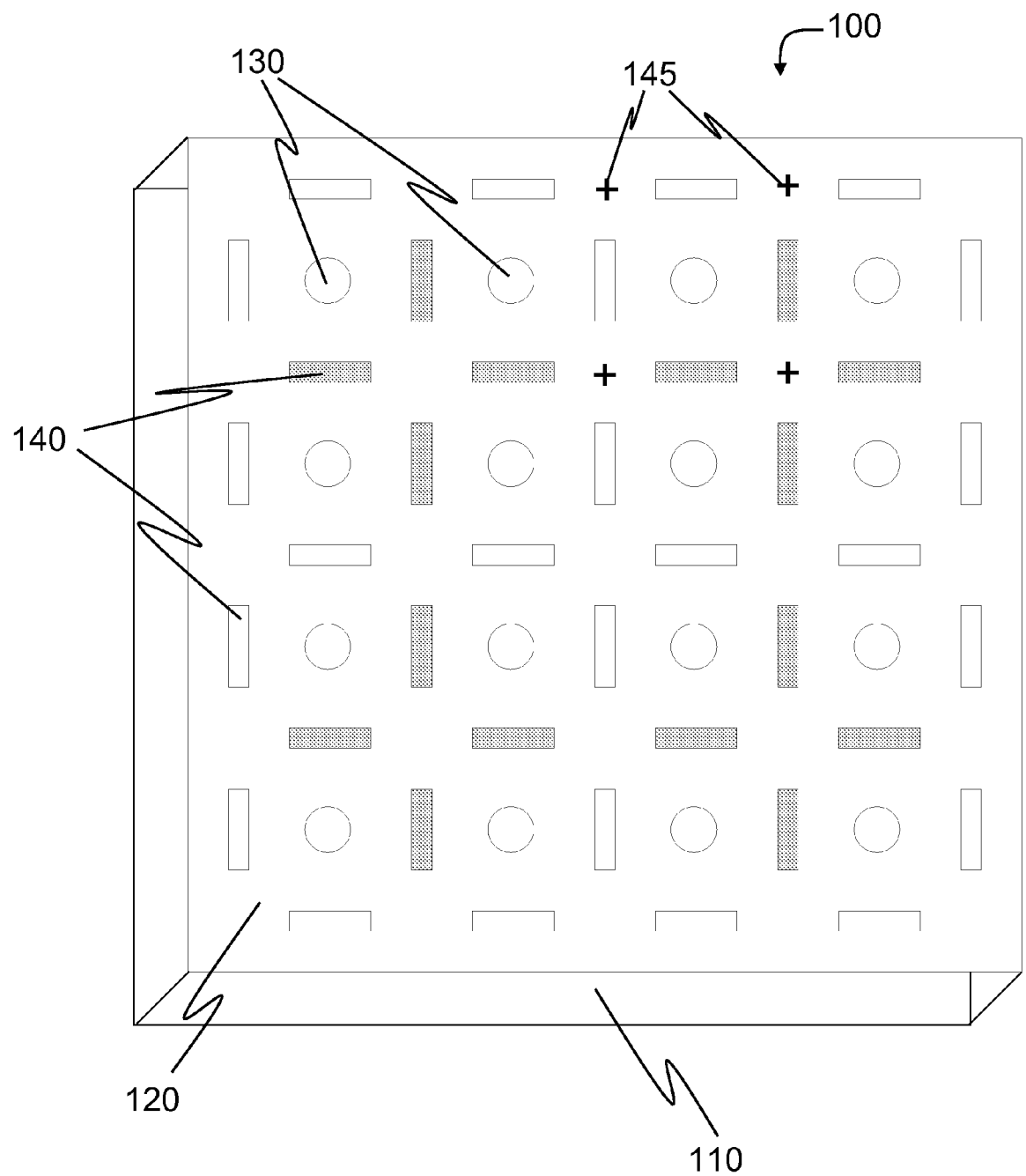
FIG. 1A is a top-down view of an apparatus for detecting molecular interactions.

FIG. 1A is a top-down view of an exemplary apparatus 100 having a sample surface and an array of sample sites 130 on the sample surface for immobilizing or functionalizing one or more substances, such as biochemical molecules or biomolecules. A biomolecule is a naturally occurring chemical compound found in living organisms. Biomolecules primarily consist of carbon and hydrogen, along with nitrogen, oxygen, phosphorus and sulfur. Proteins are one type of biomolecules found in at least some living organisms. Proteins are polymers built from amino acids, which are the building blocks used to construct larger molecules. Another type of building block is nucleotides, each of which can consist of three components: (1) either a purine or pyrimidine base, (2) a pentose sugar and (3) a phosphate group.

The immobilized biomolecules can be implemented as reagents in an assay for detecting the presence of a target substance, such as a protein. A reagent can be any substance used in chemical or biochemical reactions to bring about a desired chemical or biochemical change. An assay is a procedure where a property of a system or substance is measured. In biological science, there are various types of assays, such as antigen capture assay, bioassay, competitive protein binding assay, four-point assay, immunoassay, microbiological assay, stem cell assay, etc. For example, presence of one or more target proteins can be detected by using antibodies as reagents in an immunoassay. An immunoassay is a biochemical test that measures the level of a substance (e.g., a biomolecule) in a biological liquid using the molecular reaction of an antibody or antibodies to its antigen.

An antibody or immunoglobulin is a large Y-shaped protein used by the immune system to identify and neutralize foreign objects, such as bacterial and viruses. Each antibody contains one or more binding sites designed to recognized and bind to a specific antigen unique to the binding site. Due to the specificity of binding, antibodies are ideal candidates to use as reagents. In addition, monoclonal antibodies are often used because a monoclonal antibody binds to one binding site of a particular target molecule.

The apparatus 100 can be a biochip that includes a substrate 110 with a solid top sample surface 120. The top sample surface 120 (e.g., a sample surface or a target layer) includes multiple reagent immobilizing sample sites 130 arranged in an array and designed to immobilize reagent molecules, such as biomolecules. The substrate 110 further includes one or more calibration structures 140 deposited on the top surface 120 designed to provide on-chip calibration.

In addition, a set of alignment marks 145 can be formed on the substrate 110 of the biochip 100 to enable a scanner or imager to identify and locate a target spot (e.g., a reagent immobilizing sample site 130). These alignment marks 145 can be implemented to encode location information such as the position coordinates (x,y) of the target spots. An position encoding scheme can include a bar code, or a simple number. In some implementations, the alignment markers 145 can include markers with high image contrast for easy detection. The alignment markers 145 can so be used as alignment visual markers to guide a x-y moving stage holding a biochip to setup and configure an initial scanning position. Such alignment markers can enhance accuracy of aligning different scan data together.

Figure 1B:
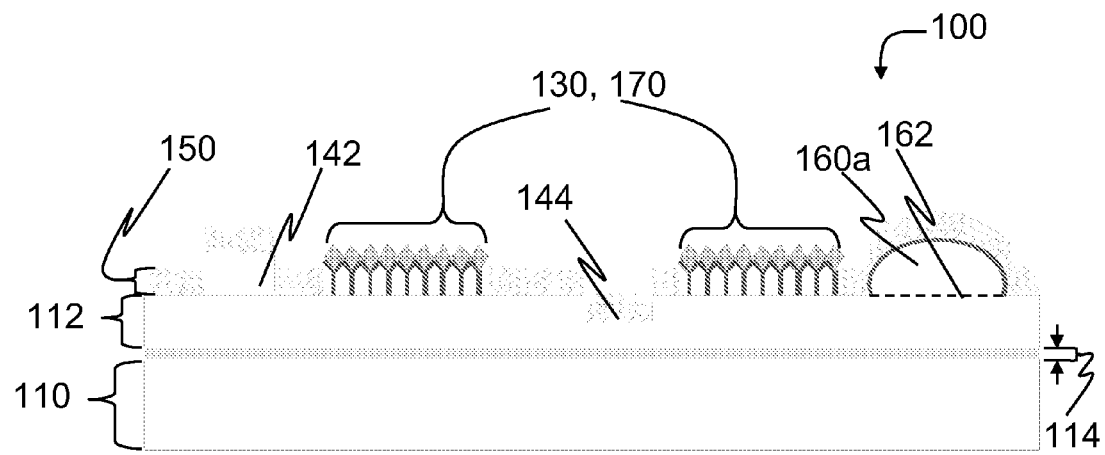
Figure 1C:
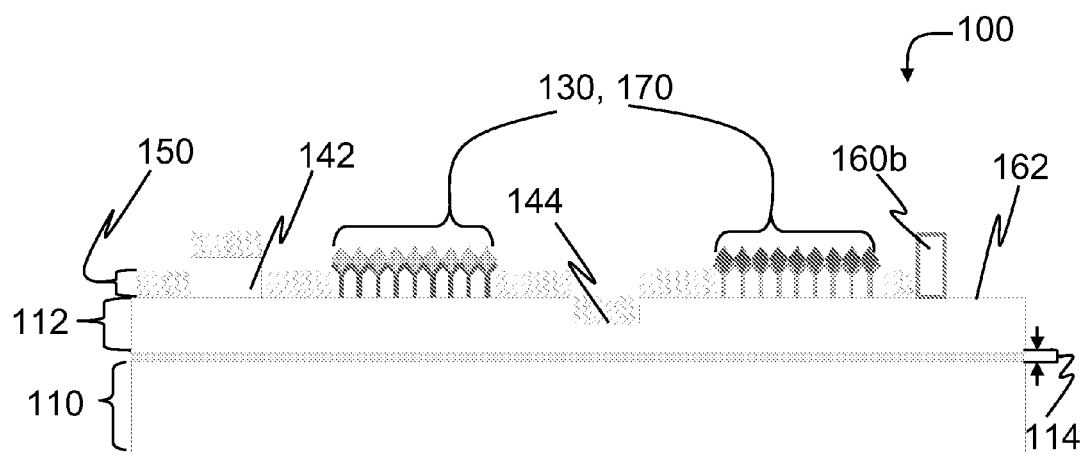

FIGS. 1B and 1C are cross sectional views of the biochip 100 in FIG. 1A. The substrate 110 of the biochip 100 can be one or more layers composed of materials having optical properties. The substrate 110 can be of a suitable thickness that can function as a support structure for the reagent immobilizing sites and/or optional thin-film layers. In some implementations the thickness of the substrate 110 can be substantially between 100 nm and 10 cm. The substrate 110 can be composed of a suitable solid dielectric material that can be polished to have a flat surface and capable of having optical quality thin-film layers deposited on top. In some implementations, the dielectric material for the substrate 110 includes various types of materials, e.g., plastic materials, glass materials, or semiconductors including Silicon (Si) and Germanium (Ge).

The biochip 100 can optionally include one or more additional optical thin-film layers 112 (e.g., sample surface or target layer) and 114 formed over the substrate 110. As illustrated in FIGS. 1B and 1C, the optically structured substrate 110 includes an additional thin-film layer 112 composed of a transparent material that allows light to at least partially pass through the layer. The transparent thin-film layer 112 can have a thickness that is substantially between 100 nm and 1000 nm. The transparent thin-film layer can be composed of any solid dielectric material which is optically transparent in the wavelength range of a probe beam of light. The dielectric material for the transparent thin-film layer 112 can include, e.g., various types of glass and semiconductors, such as Si and Ge, etc. In some implementations, the transparent layer 114 can be composed of material similar to the substrate 110. The transparent thin-film layer 112 is deposited or grown on a surface of the substrate 110. Typical deposition processes includes, but not limit to, e-beam deposition, sputter, chemical vapor deposition (CVD), plasma enhanced (PE-CVD), and etc. The difference in the index of refraction between the substrate 110 material and the top surface material provides boundary reflection when illuminated with a probe beam of light. For example, silicon to air interface can provide substantially 20% reflection.

In designs where the optical index of refraction for the substrate 110 is similar to the optical index of refraction for the transparent thin-film layer 112, a second thin-film layer 114 can be deposited between the substrate 110 and the transparent thin-film layer 112. The second thin-film layer 114 is a thin reflective layer composed of a material that at least partially reflects light. The reflective thin-film layer can have a thickness that is substantially between 1 nm and 200 nm. The reflective thin-film layer 114 is deposited between the substrate 110 and the transparent thin-film layer 112 to enhance the boundary reflection between the transparent thin-film layer 112 and the substrate 110. The reflective thin-film layer 114 can be composed of material with good optical properties in the wavelength range of the probe beam of light in the detection system. The reflective thin-film layer 114 has an optical index of refraction different than the substrate 110 and the reflective thin-film 112. The material for the reflective thin-film layer can be a number of materials, including, e.g., Titanium dioxide ($TiO_2$), Tantalum pentoxide ($Ta_2O_5$), and others. Because $TiO_2$ has a high refractive index (n≈2.4), $TiO_2$ is an excellent reflective optical coating for dielectric substrate when deposited as a thin-film. Tantalum pentoxide is also a high refractive index (i.e., low absorption) material useful as coatings for reflecting light in the near-UV to IR spectra regions.

FIGS. 1B and 1C also show reagent immobilizing sites 130 with reagents 170 (e.g., antibodies) localized to the reagent immobilization sites 130. The dielectric material, such as glass, of the transparent thin-film layer 112 provides a passive surface for the reagents 170 to absorb and bind. Using surface chemistry, the reagent immobilizing sites 130 can be activated to promote immobilization of biomolecules on the sites 130. Various techniques for activating a passive surface to immobilize biomolecules can be used to implement the biochip 100. Some examples of such techniques are described in Immobilized Biomolecules in Analysis: A Practical Approach. Edited by Tony Cass and Frances S. Ligler. New York. Oxford University Press, 1998.

As specific examples for the calibration structures 140 in FIG. 1A, two types of calibration structures or reference steps 142 and 144 are shown in FIGS. 1B and 1C. The first calibration structure 142 is a positive structure having a known thickness or height that extends beyond the height at the reagent immobilizing sites 130. The positive calibration structure 114 of a known height can be composed of a solid dielectric material with good optical properties, such as various types of glass, plastic, and semiconductors. The positive calibration structure 112 can be implemented by depositing a dielectric layer with a top surface as the calibration surface at a known height on top of the substrate. The second calibration structure 144 is a negative structure having a known thickness or height that is lower than the height at the reagent immobilizing sites 130. The negative calibration structure 144 can be implemented by etching away a selected portion of the transparent thin-film layer 112 to create a pit or well of a known height where the bottom surface of the pit or well is the calibration surface. In some implementations, these optional calibration structures are created with photolithography and thin film deposition. These reference steps can be used to provide optical reference signals under illumination of probe light and the optical reference signals can be used correct certain inaccuracies or errors in measurement, e.g., inaccuracies or errors caused by instrumentation drift, liquid properties changes, or environmental factors (for example temperature change).

In some implementations, either the positive references 142 or the negative references 144 may be sufficient for calibration. The use of both positive references 142 and the negative references 144 can be advantageous in other implementations because these two different types references can provide a wider range in the thickness calibration and thus improve the calibration accuracy.

When illuminated with a probe of light, multiple reflected light beams can be generated from different locations on the biochip 100, e.g., reflections at different interfaces or boundaries between the substrate 110 and the thin-film layers 112 and 114. These reflected light beams can be detected and processed for optical measurement of one or more samples on the biochip 100. The reflected light beams at one location on the biochip 100 (e.g., a particular sample site 130) can optically interfere and such interference can be used to generate an interference signal with a spectrum distribution within the spectral bandwidth of the probe light. Based on the spectrum distribution generated, height information at the location of the biochip 100 can be determined. Such interference signals can be obtained at different locations of the biochip and thus the height information at different locations (e.g., different sample sites 130) can be obtained. The height information at each sample site 130 can be further processed to identify the immobilized molecules the sample site 130. Different sample sites 130 can be functionalized to immobilize different target molecules and thus a single chip can be used to simultaneously measure different target molecules.

Optical interference is an effect that occurs when two coherent or partially coherent waves (or beams of light) at an equal frequency or two similar frequencies are spatially superimposed. This can happen when light rays from a single source travel by different paths to the same point. If, at the point of meeting, the two waves are in phase (vibrating in unison, and the crest of one coinciding with the crest of the other), they will constructively interfere and combine to form a new wave and the amplitude of the new wave is the sum of the amplitudes of the original waves. If the two waves meet at a location and are out of phase (e.g., the crest of one coinciding with a trough of the other), the result is a wave whose amplitude is the difference of the original amplitudes. This process is called destructive interference. If the original waves have equal amplitudes, they may completely destroy each other, leaving no wave at all. Constructive interference results in a bright spot, an destructive interference produces a dark spot. Partial constructive or destructive interference results whenever the waves have an intermediate phase relationship. Two waves interfere only if their phase relationship does not change (i.e., coherent). In contrast, light waves from two different sources do not interfere because radiations from different atoms are constantly changing their phase relationships (i.e., non-coherent.)

The use of optical interference on the biochip 100 to optically measure different sample sites 130 can provide highly sensitive measurements of the thickness of target molecules interacting with immobilized reagents at each sample site 130 and thus can be used to determine presence or absence of the target molecules at each sample site 130. Notably, this optical technique, by itself, does not require a fluorescent labeled substance to be attached to the target molecules and/or secondary labeled reagents to be mixed in a sample solution using various optical fluorescent techniques, and thus this technique does not chemically or biologically alter the sample under measurement. Hence, one of the applications of the biochip 100 is to provide label-free and sensitive optical measurement of a sample to identify presence or absence of certain target molecules of the sample. In other applications, such a biochip 100 and the optical interference technique may be combined with other fluorescent labeled assay techniques.

In some implementations, the calibration structures can become contaminated with foreign particles (e.g., biomolecules) and thus provide inaccurate reference height measurements. To combat such inaccuracies, additional reference structures 160a and 160b can be implemented as shown in FIGS. 1B and 1C. Reference structure 160a is composed of a thick dielectric material having an optical index of refraction different than the material for the reflective thin-film layer 112. The material for the reference structure 160a can include materials having different index of refraction than glass, such as a drop of epoxy, etc. This protective layer is thicker than one wavelength of the light (or the coherent length of the light) used to probe the biochip, so the local interference of reflected light occurs only between the light beams reflected from transparent thin-film layer. Since the reference structure 160a is deposited on top of the clean surface 162, the clean surface 162 is protected from contamination. Thus, variations in height measurements due to contamination at the clean surface 112 can be minimized or avoided. For example, the effect of any substance (e.g., biomolecules) absorbed on top of the protective layer can be minimized. Alternatively, the reference structure 160b can be a physical barrier of a known shape and height designed to prevent foreign substances (e.g., biomolecules) from contaminating the clean surface 162.

In order to promote binding of reagents to the reagent immobilizing sites 130 only, an optional protective layer 150 can be deposited on top. The protective layer 150 functions to localize the reagents to the reagent immobilizing sites 130. The protective layer 150 is composed of materials known to resist adhesion of biomolecules (e.g., proteins). The material for the biomolecule resistant layer 150 can include a high density polyethylene glycol (PEG), Dextran, and etc. PEG is prepared by polymerization of ethylene oxide and is known to resist protein adhesion. Dextran is a complex, branched polysaccharide made of many glucose molecules joined into chains of varying lengths. Similar to PEG, Dextran also resists biomolecule adhesion. Alternatively, other suitable materials with biomolecule resistant properties can be implemented. At the locations where biochemical molecules will be immobilized a laser beam can used to remove the polymer film, so different molecule immobilization chemistry can be apply to the glass substrate to immobilize biochemical molecules of interests. At all other regions of the surface 120, the protective layer 150 minimizes absorption of biomolecules.

Figure 1D:
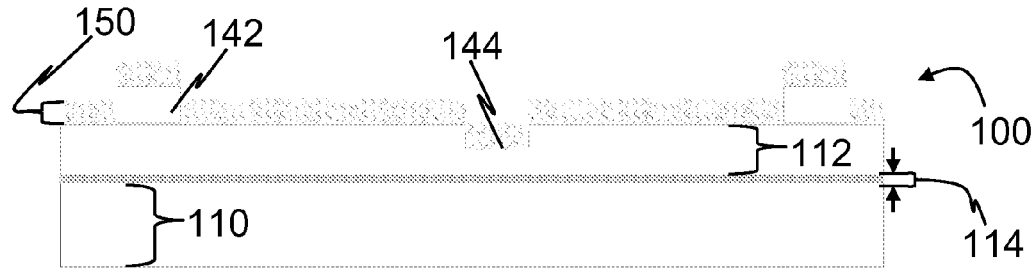
Figure 1E:
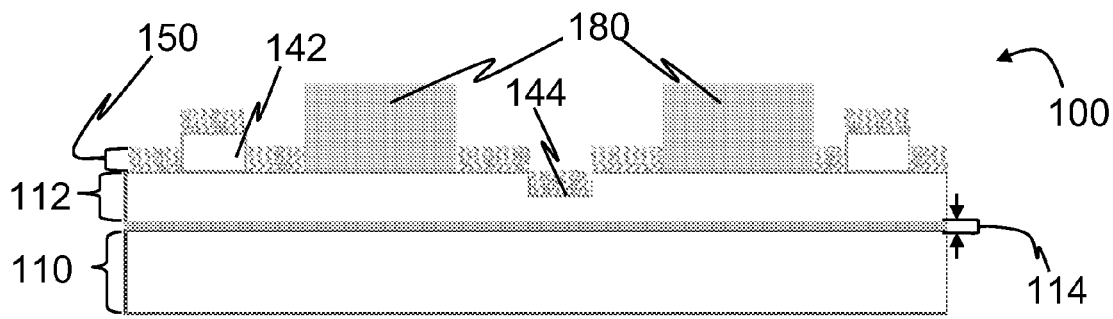
Figure 1F:
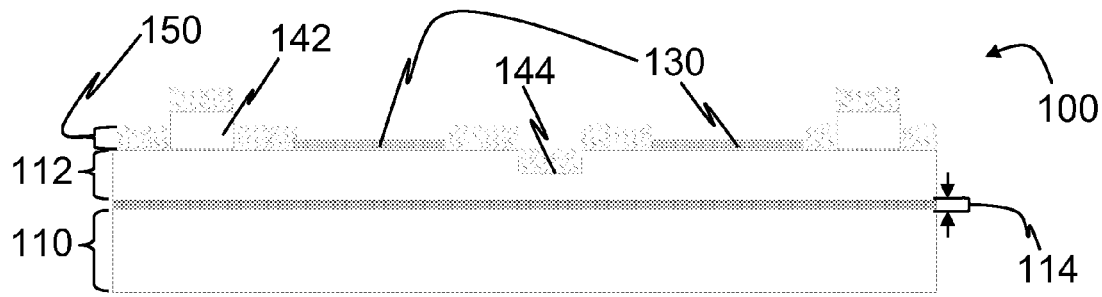
Figure 1G:
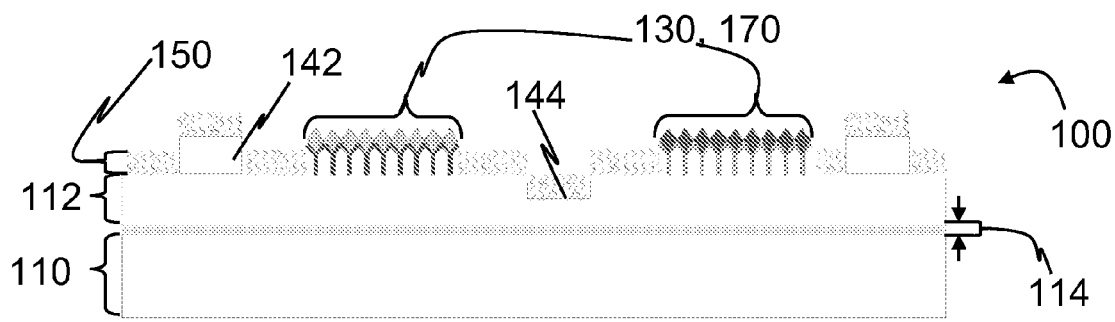

FIGS. 1D, 1E, 1F, and 1G are additional cross sectional views of a biochip 100 for illustrating a process of creating reagent immobilizing sites 130. FIG. 1D shows the biochip 100 including a substrate 110, a reflective thin-film layer 114 deposited on top of the substrate 110, and a transparent thin-film layer 112 deposited on top of the reflective thin-film layer 114. On top of the transparent thin-film layer 112 a protective layer 150 can be deposited to resist adhesion of biomolecules to the top surface of the biochip 100. FIG. 1E shows laser beams 180 applied to one or more target locations on the biochip surface to etch away the protective layer 150 and expose the passive surface of the transparent thin-film layer 112. Alternatively, other etching techniques, such as plasma etching or chemical etching can be implemented. In some implementations, the protective layer 150 can be deposited at all areas other than the desired reagent immobilization sites 130. FIG. 1F shows the resultant reagent immobilizing sites 130 created by laser etching. FIG. 1G shows reagents 170 immobilized to the reagent immobilizing sites 130.

Biochip Implementations

Figure 2A:
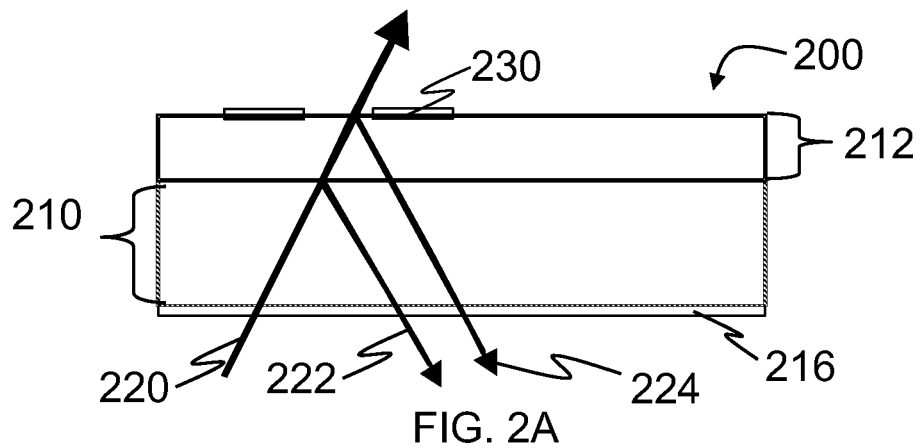
FIGS. 2A, 2B and 2C are cross sectional views of a biochip having a substrate and a transparent thin-film layer.

FIG. 2A is a cross sectional view of a biochip 200 having a substrate 210 and a transparent thin-film layer 212. Because the refractive index of the thin-film layer 212 is different from the refractive index of the substrate, an optional reflective thin-film layer is not implemented. The biochip 200 is illuminated by a probe beam of light 220 originating from a light source (not shown) located below the substrate 210. An optional antireflective coating 216 can be disposed on the opposite surface of the optical substrate 210 where molecule is immobilized. The antireflective coating enhances the signal of the reflected beams of light 222 and 224 by allowing more light to pass through the substrate 210. A first reflected light beam 222 is reflected off the boundary between the substrate 210 and the thin-film layer 212. Also, a second reflected light beam 224 is reflected off the top surface of the thin-film layer 212. Based on the reflected beams 222 and 224 a spectrum image is generated. The generated spectrum image is used to obtain height information at different locations at the top surface of the biochip 200 before reagents are immobilized on the reagent immobilizing sites 230.

The probe beam of light 220 incident on the top surface of the biochip 200 reflects off different layer interfaces (e.g., reflected beam 222 off the interface between the substrate 210 and the transparent thin-film layer 212; reflected beam 224 off the interface between the transparent thin-layer 212 and air). The multiple reflected light beams 222 and 224 cause interference, and such interference causes spectral distribution of the reflected light beams 222 and 224. The minimum and the maximum of the spectral distribution are detected to calculate the film thickness using Equations (1)-(2).

$$I_r = I_1 + I_2 + 2I_1I_2\cos\left(2\pi\frac{2nd}{\lambda}\right) \quad (1)$$

$I_r$=composite light beam intensity from multiple reflected light beams
$I_1$=reflected beam of light off a first layer interface
$I_2$=reflected beam of light off a second layer interface
n=optical index of the light path material
d=distance between two reflective interface surfaces
at minimum or maximum of the spectral distribution, $$dn = \frac{m\lambda_m}{2} \quad (2)$$

m=an integer (e.g., from 1 to 200) that represents the mode of interference

Figure 2B:
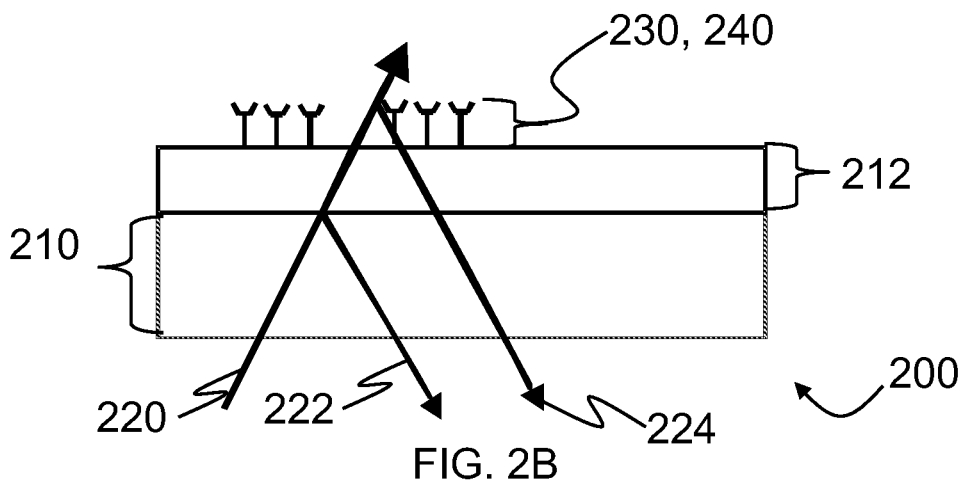

FIG. 2B is a cross sectional view of the biochip 200 with reagents 240 immobilized at the reagent immobilizing site 230. The first reflected beam 222 is reflected off the boundary between the substrate 210 and the thin-film layer 212 as before with respect to FIG. 2A. The path of the second reflected beam 224 reflected off the reagent immobilizing site 230 is changed due to the presence of the immobilized reagents 240. This change in the light path of the second reflected beam 224 is calculated as height increases due to the immobilized reagents 240.

Figure 2C:
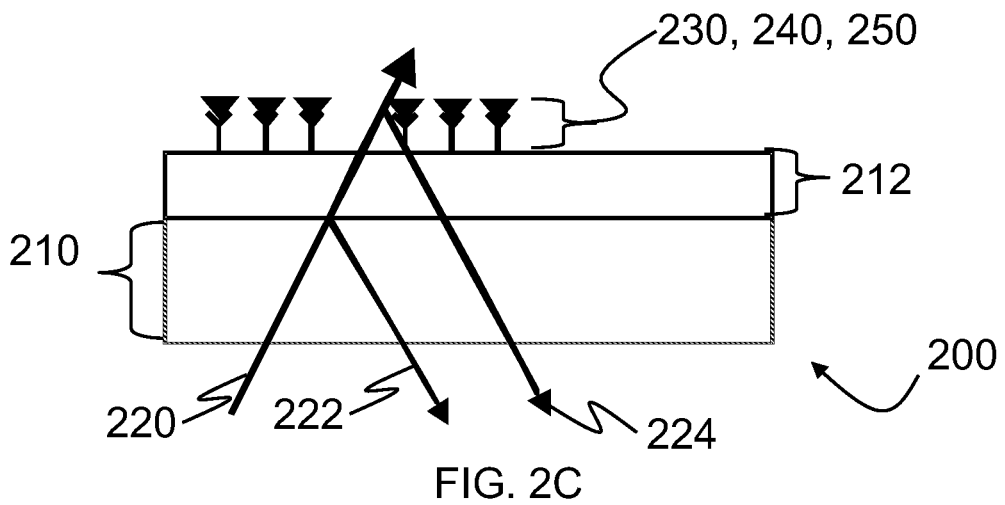

FIG. 2C is a cross sectional view of the biochip 200 having sample biomolecules 250 interacting with reagents 240 at the reagent immobilizing site 230. The first reflected beam 222 is reflected off the boundary between the substrate 210 and the thin-film layer 212 as before with respect to FIGS. 2A and 2B. The second reflected beam 224 reflected off the reagent immobilizing site 230 is changed by the interactions between the sample biomolecules 250 and the immobilized reagents 240. This change in the light path of the second reflected beam 224 is calculated as height increases due to the molecular interactions between the sample biomolecules 250 and the reagents 240 at the reagent immobilizing sites 230 (See process with respect to FIGS. 5-7 for further description on detecting molecular interactions.)

Figure 3A:
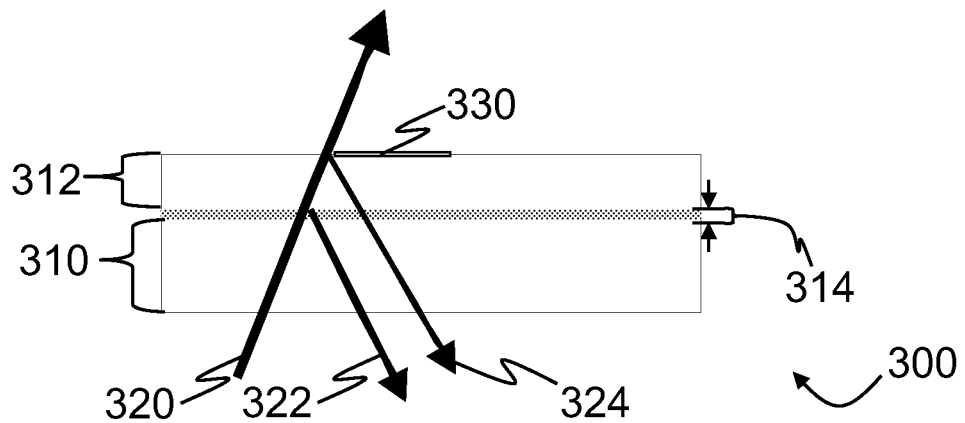
FIGS. 3A, 3B and 3C are cross sectional views of a biochip having a substrate, a transparent thin-film layer and a reflective layer.

FIG. 3A is a cross sectional view of a biochip 300 having a substrate 310 and a transparent thin-film layer. An optional reflective thin-film layer 314 is deposited between the substrate 310 and the transparent thin-film layer 312 in implementations when the refractive index of the substrate 310 is similar to the transparent thin-film layer 312. The biochip 300 is illuminated by a probe beam of light 320 originating from a light source (not shown) located below the substrate 310. A first reflected light beam 322 is reflected off the reflective thin-film layer 314. Also, a second reflected light beam 324 is reflected off the top surface of the thin-film layer 312. The reflected beams 322 and 324 are analyzed to obtain height information of the substrate 310 and the thin-film layer 312 before immobilizing reagents on the reagent immobilizing sites 330. The process of analyzing the reflected beams of light 322 and 324 to obtain height information is described with respect to FIG. Y.

Figure 3B:
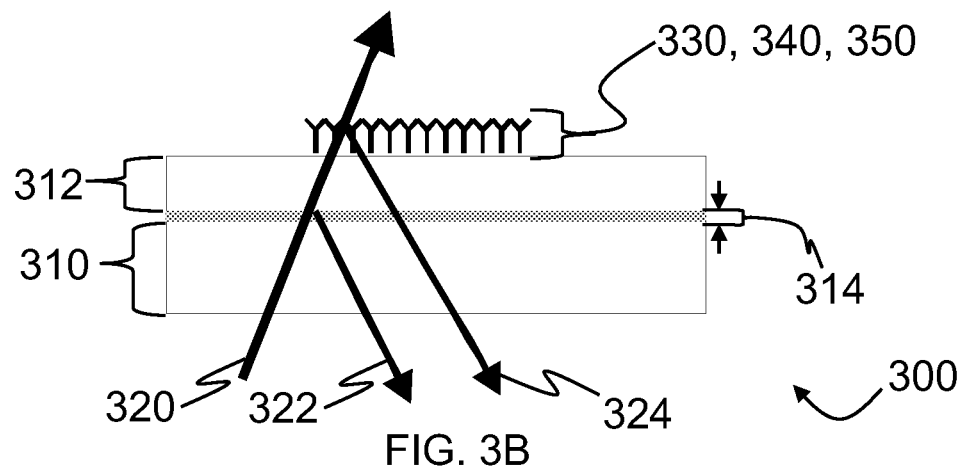

FIG. 3B is a cross sectional view of the biochip 300 with reagents 340 immobilized at the reagent immobilizing site 330. The first reflected beam 322 is reflected off the reflective thin-film layer 314 as before with respect to FIG. 3A. The second reflected beam 324 reflected off the reagent immobilizing site 330 is changed due to the presence of the immobilized reagents 340. This change in the light path of the second reflected beam 324 is calculated as height increases due to the immobilized reagents 340 (See process with respect to FIG. Y for further description on detecting molecular interactions.)

Figure 3C:
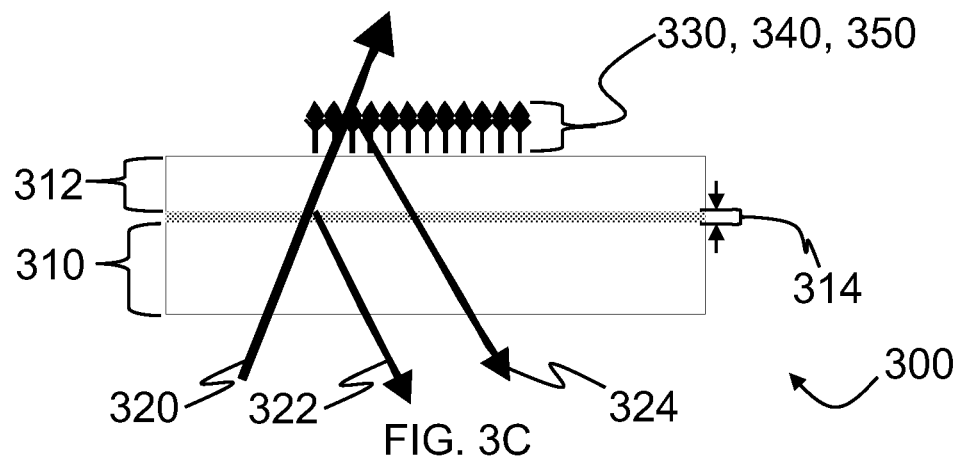

FIG. 3C is a cross sectional view of the biochip 200 having sample biomolecules 350 interacting with reagents 340 at the reagent immobilizing site 330. The first reflected beam 322 is reflected off the reflective thin-film layer 314 as before with respect to FIGS. 3A and 3B. The second reflected beam 324 reflected off the reagent immobilizing site 330 is changed by the interactions between the sample biomolecules 350 and the immobilized reagents 340. This change in the light path of the second reflected beam 324 is calculated as height increases due to the molecular interactions between the sample biomolecules 350 and the reagents 340 at the reagent immobilizing sites 330 (See process with respect to FIG. Y for further description on detecting molecular interactions.)

Figure 4:
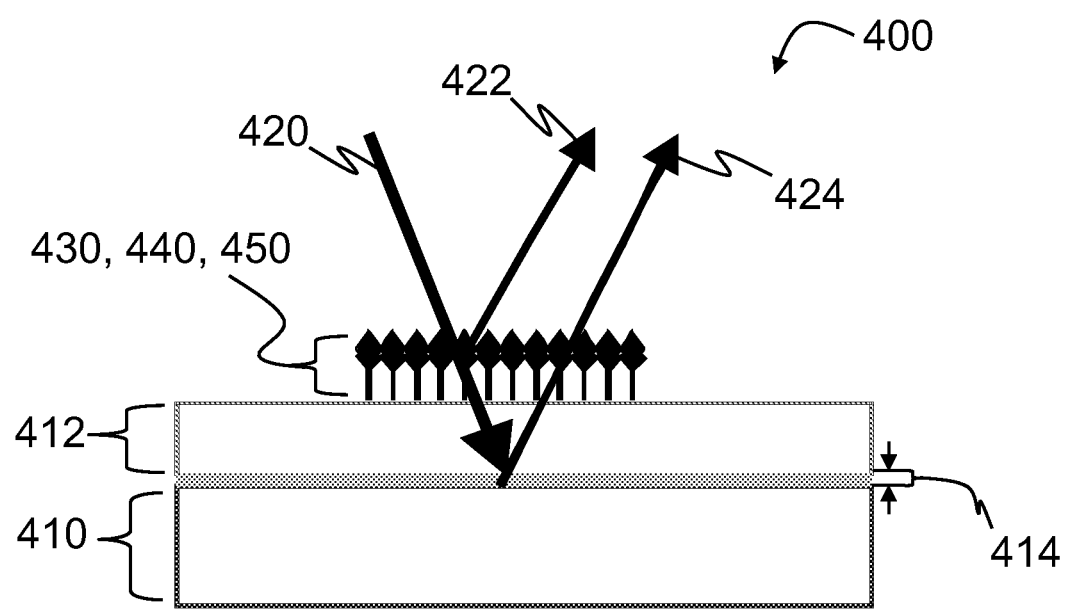
FIG. 4 is a cross sectional view of a biochip showing a probe beam of light originating from above the biochip.

While FIGS. 2A, 2B, 2C, 3A, 3B and 3C show the probe beam of light 220 and 320 originating from below the substrate, in some implementations, the biochip 200 and 300 can be illuminated with a probe beam of light originating from above the substrate 210 and 310. FIG. 4 is a cross sectional view of a biochip 400 including a substrate 410, and a transparent thin-film layer 412. An optional reflective thin-film layer 414 can be deposited between the substrate 410 and the transparent thin-film layer 412 in implementations when the refractive index of the substrate 410 is similar to the transparent thin-film layer 412. The biochip 400 is illuminated by a probe beam of light 420 originating from a light source (not shown) located above the substrate 410. A first reflected light beam 422 is reflected off the reflective thin-film layer 414. Also, a second reflected light beam 424 is reflected off various locations on the top surface of the thin-film layer 412. The second reflected beam 424 reflected off the reagent immobilizing site 430 is affected by the interactions between the sample biomolecules 450 and the immobilized reagents 440. The molecular interactions results in a change in the light path of the second reflected beam 424, which is calculated as height increases, at the reagent immobilizing site 430. Thus, the location of the probe beam of light 420 (either below or above the substrate 410) can be varied. (See process with respect to FIG. Y for further description on detecting molecular interactions.)

Figure 5:
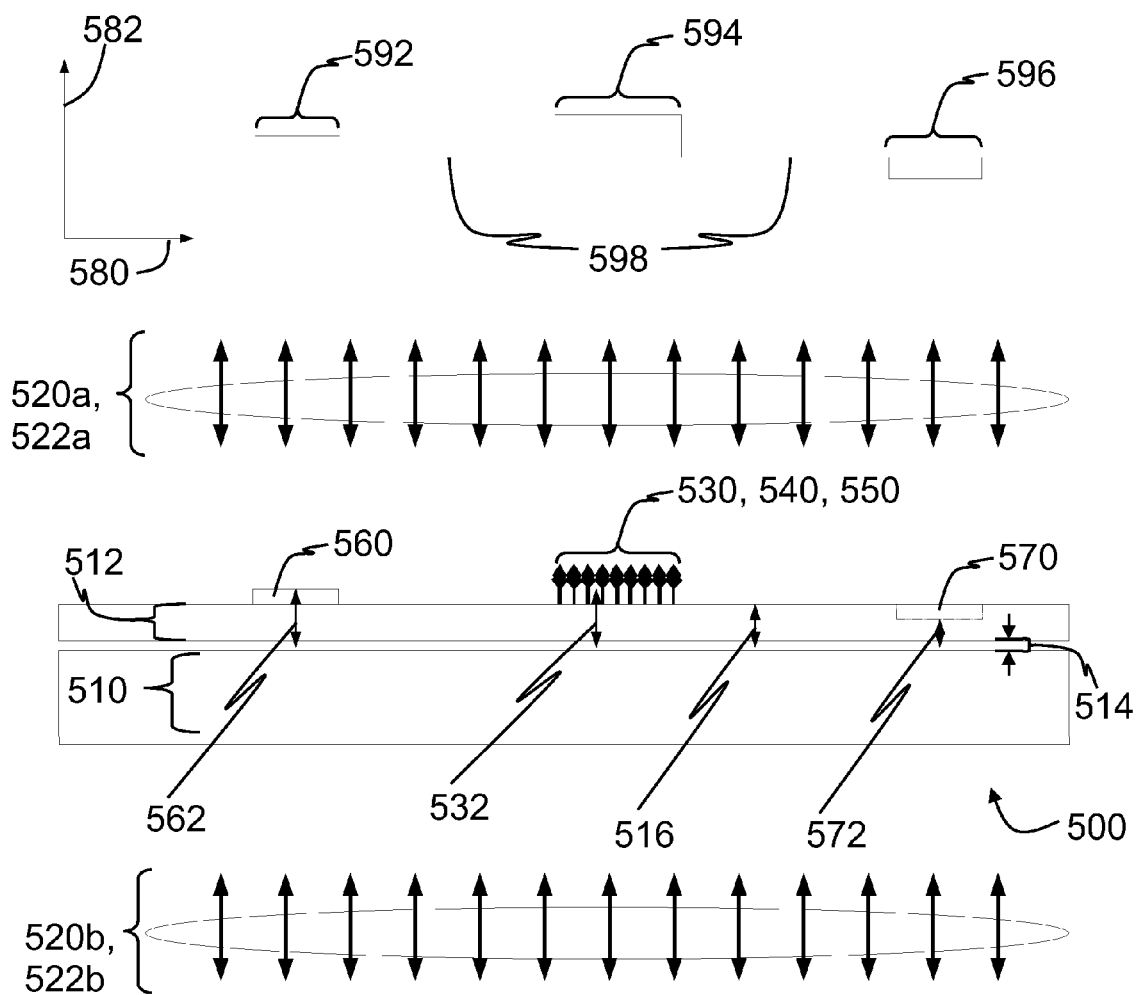
FIG. 5 is a cross sectional view of a biochip with corresponding signal depth profiles.

FIG. 5 is a cross sectional view of a biochip 500 with a corresponding reflected light signal profile. The biochip 500 includes a substrate 510, a transparent thin-film layer 512 and a reflective thin-film layer 514. The biochip also includes a positive calibration structure 560 and a negative calibration structure 570. Further, the biochip includes one or more reagent immobilizing sites 530 with sample biomolecules 550 interacting with the immobilized reagents 540.

When illuminated by a probe beam of light 520a (from below the substrate 510) or 520b (from above the substrate 510), reflected beams of light 522a or 522b reflected from various locations 516, 532, 562, and 572 along the X-axis 580 on the biochip surface are captured and analyzed to obtain a spectrum image of the biochip 500 surface that provides spectral distribution of the reflected light beams 522a or 522b. At location 516, the normal height or thickness, Tnorm, of the transparent thin-film layer 512 is measured. At location 532, the height or thickness, Tspot, of the reagent immobilizing sites 530 is measured. Tspot includes the normal height of the transparent thin-film layer 512 affected by the presence of reagents 540 and/or sample biomolecules 550 interacting with the reagents 540. At location 562, the height or thickness of the positive calibration structure 560, Tstep1, is measured. Tstep1 is the sum of Tnorm and the known height or thickness of the positive calibration structure 560. At location 572, the height or thickness of the negative calibration structure 570, Tstep2, is measured. Tstep2 is Tnorm reduced by the known negative height of the negative calibration structure 570.

The reflected beams of light 522a and 522b reflected off locations 516, 532, 562, and 572 are shown as corresponding depth profile signals 598, 594, 592, and 596. represented as distances to a light probe (not shown) 582 with respect to the X-axis coordinates of the locations 516, 532, 562 and 572. Notice that signal 598 represents the normal height or thickness, Tnorm, of the transparent thin-film layer 512; signal 594 represents the height or thickness at the reagent immobilizing site 530, Tspot; signal 592 represents the height or thickness at the positive calibration structure 560, Tstep1 (which is a combined height of the transparent thin-film layer 512 and the known height of the positive calibration layer 560); and signal 596 represents the height or thickness at the negative calibration structure 570 (which is the normal height of the transparent thin-film layer 512 reduced by the negative height of the negative calibration structure 570.)

In some implementations, the calibration structures (e.g., 140) are not deposited on the target transparent thin-film layer. Alternative to using the calibration structures 140 to determine a height or thickness of the target transparent thin-film layer, a surface with non-specific binding can be used. A surface of the transparent thin-film layer that is not being used to immobilize reagent molecules can serve the functions of the calibration structures 140. The known height or thickness of the transparent thin-film layer can provide a known height or thickness information used to determine the height at the reagent immobilization sites (e.g., 130) as described with respect to FIGS. 6-7.

Figure 6:
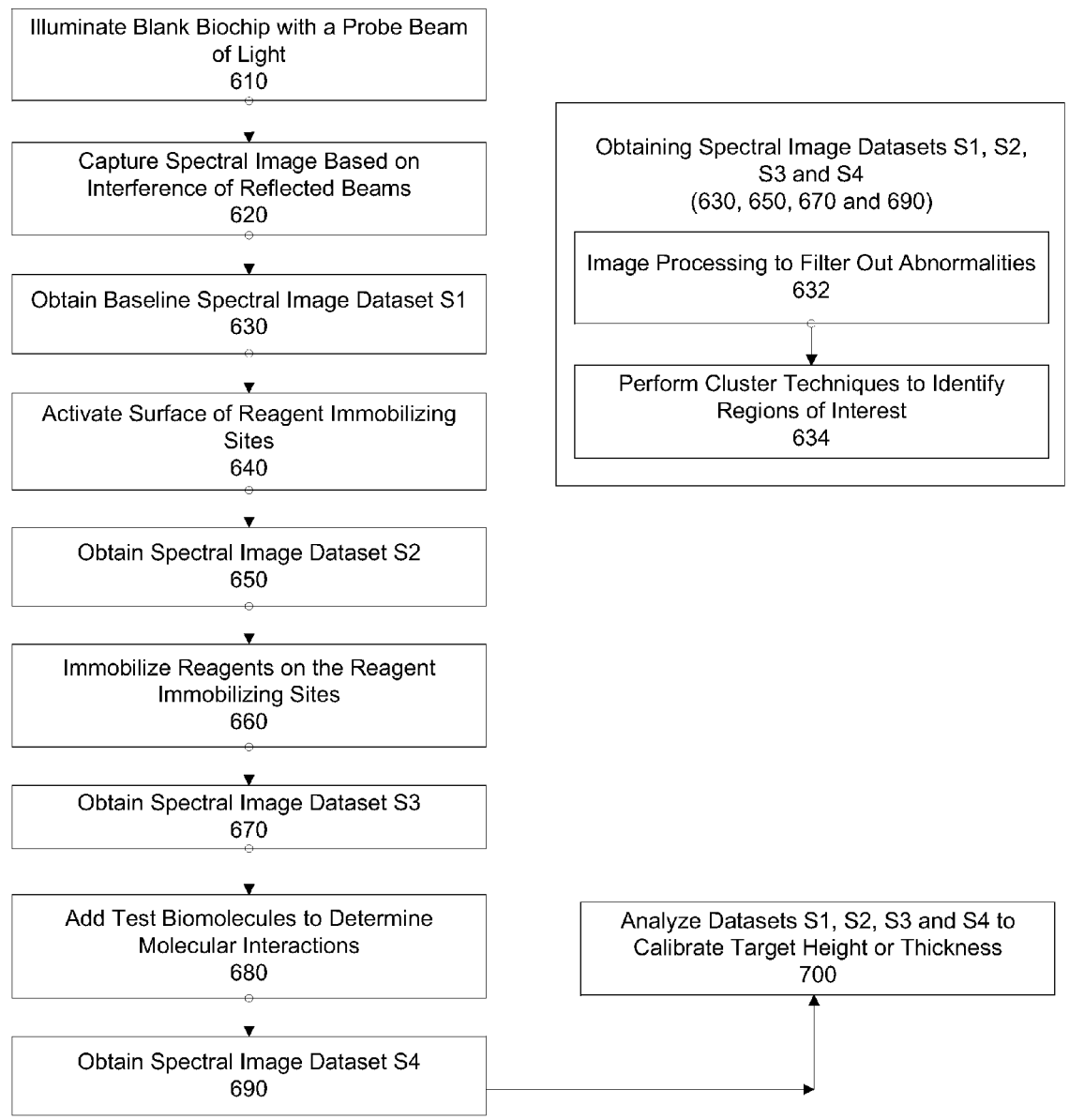
FIG. 6 is a flow chart of a process for detecting molecular interactions.

FIG. 6 is a flow chart of an exemplary process for determining the height or thickness of the transparent thin-film layer 512 of the biochip 500 to detect target molecules based on molecular interactions between the immobilized reagent molecules at the reagent immobilizing sites 530 and the target molecules in a sample solution applied to the reagent immobilizing sites 530. A blank biochip is illuminated using a probe beam of light at 610. Initial measurement to capture a spectrum image, based on the reflected beams of light 522a or 522b, is performed at 620. The captured spectrum image is analyzed to obtain a baseline spectrum image dataset, S1 at 630. Spectrum image dataset S1 includes Tspot_1 (thickness information at reagent immobilizing site 530), Tstep1_1 (thickness information at positive calibration structure 560), Tstep2_1 (thickness information at negative calibration structure 570) and Tnorm_1 (thickness information of transparent thin-film layer 512). The notation "_1" represents the corresponding dataset.

Obtaining the spectrum image dataset S1 (and other captured spectrum image datasets) includes image processing 632 and clustering 634. The spectrum image captured based on interference of reflected beams are filtered using standard image processing (e.g., a digital filter) at 632. Image processing technique can be use to detect any defects and abnormalities in the spectrum image (e.g., dusts on the transparent thin-film layer surface, immobilization defects at target spot, etc.) Abnormalities can cause the measured height or thickness to be unusually high or low. After filtering out the abnormalities and/or defects, cluster techniques can be used to select clusters of image pixels that represent various regions of interest at 634. The regions of interest includes the target spot 532 (at reagent immobilizing sites 530), reference steps 562, 572 (at positive and negative calibration structures 560 and 570 respectively), and normal planar surface 516. The thickness measurements are repeated and averaged for each cluster to obtain Tspot, Tstep1, Tstep2, and Tnorm. These thickness readings are used to calculate final target spot thin-film layer thickness.

At 640, the blank biochip is treated to activate the surface at the reagent immobilizing site 520. A second spectrum image dataset S2 is obtained at 650 to determine the effect of the surface activation on the thickness. Dataset S2 includes Tspot_2, Tstep1_2, Tstep2_2 and Tnorm_2. Reagents are immobilized onto the activated reagent immobilizing sites at 660. A third spectrum image dataset S3 is obtained at 670 to determine a change in the thickness caused by the reagents. Dataset S3 includes Tspot_3, Tstep1_3, Tstep2_3 and Tnorm_3. A sample solution containing target biomolecules are added to the reagent immobilizing sites at 680 to allow molecular interactions to occur between the reagents and the target biomolecules. A fourth spectrum image dataset, S4, is obtained at 690 to determine a change in the thickness caused by molecular interactions. Dataset S4 includes Tspot_4, Tstep1_4, Tstep2_4, Tnorm_4.

Each of the positive and negative calibration structures are designed to have a known shape and thickness (or height or depth) that are constant. Such known thickness provides a reference thickness or height measurement that can be used to calibrate the thickness measurements at the desired target location (e.g., reagent immobilization sites 530) at 700.

Figure 7:
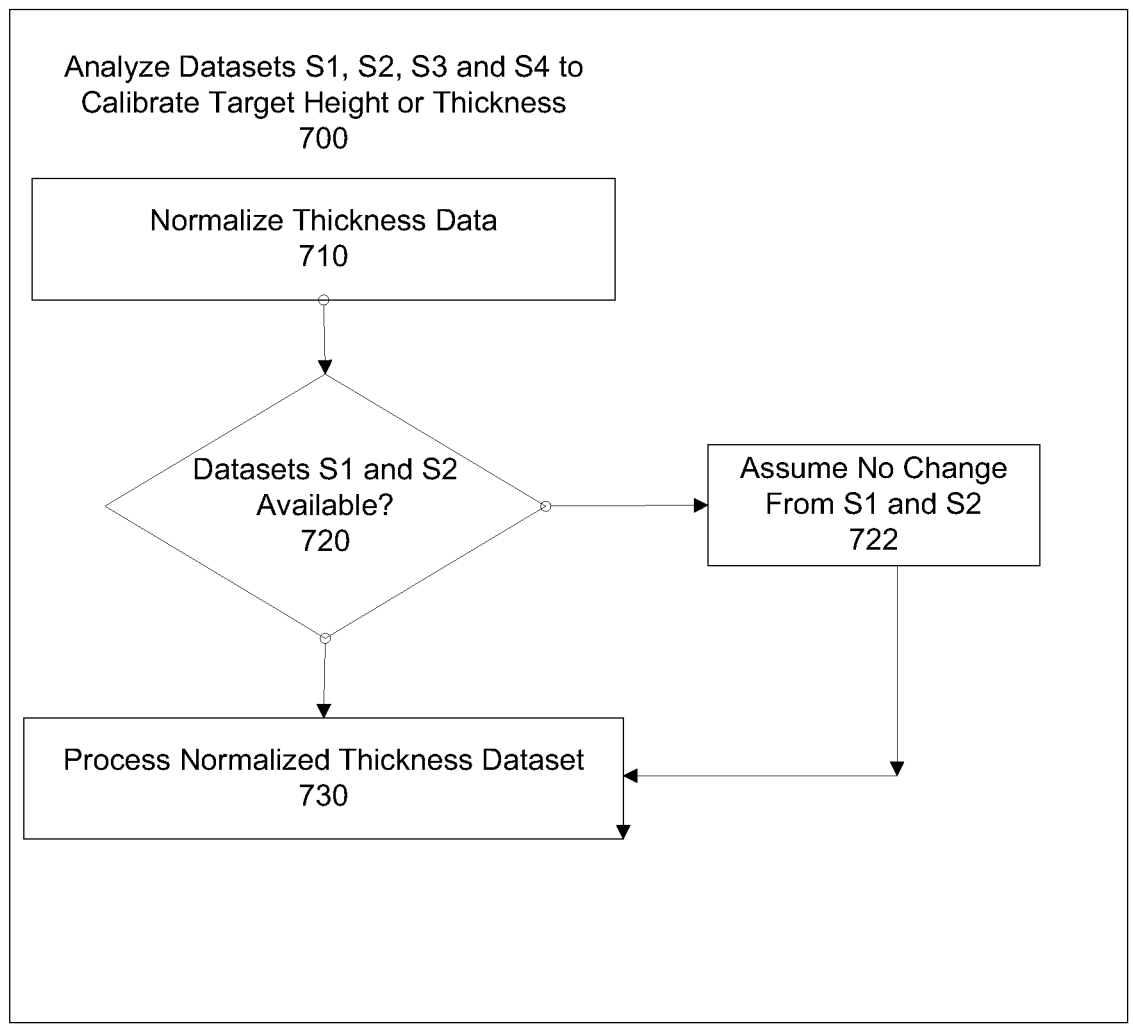
FIG. 7 is a flow chart of a process for analyzing thickness or height data.

FIG. 7 is a flow chart illustrating one exemplary process for the height or thickness calibration 700 in detail. At 710, the normalized thickness or height at the positive calibration structure, ST1, the negative calibration structure, ST2, and the reagent immobilizing site, SP, are determined using Equations (3a)-(6c).

$$S1: ST1\_1 = Tstep1\_1 - Tnorm\_1 \qquad (3a)$$

$$ST2\_1 = Tstep2\_1 - Tnorm\_1 \qquad (3b)$$

$$SP1 = Tspot\_1 - Tnorm\_1 \qquad (3b)$$

$$S2: ST1\_2 = Tstep1\_2 - Tnorm\_2 \qquad (4a)$$

$$ST2\_2 = Tstep2\_2 - Tnorm\_2 \qquad (4b)$$

$$SP2 = Tspot\_2 - Tnorm\_2 \qquad (4c)$$

$$S3: ST1\_3 = Tstep1\_3 - Tnorm\_3 \qquad (5a)$$

$$ST2\_3 = Tstep2\_3 - Tnorm\_3 \qquad (5b)$$

$$SP3 = Tspot\_3 - Tnorm\_3 \qquad (5c)$$

$$S4: ST1\_4 = Tstep1\_4 - Tnorm\_4 \qquad (6a)$$

$$ST2\_4 = Tstep2\_4 - Tnorm\_4 \qquad (6b)$$

$$SP4 = Tspot\_4 - Tnorm\_4 \qquad (6c)$$

At 720, a determination is made whether all four datasets S1, S2, S3 and S4 are available. If only S3 and S4 are available, the positive calibration structure 560 and the negative calibration structure 570 are assumed to have not changed from S1 to S2 at 722. Any difference between S1 and S2 can be contributed to the measurement system drift or other unknown factors. These known factors are also assumed to affect the target spot, SP 532, measurement (at the reagent binding sites 530) in the same way from S1 through S4. In addition, such effect of the known system factors are assumed to be small compared to the height measurement.

At 730, the calibrated or normalized spectrum datasets S1, S2, S3, and S4 are processed to determined the change in the thickness of the transparent thin-film layer 512 due to molecular interactions using Equations (7a)-(10).

$$Us = (ST1\_4 - ST1\_3)/ST1\_4 \qquad (7a)$$

$$Us = (ST2\_4 - ST2\_3)/ST2\_4 \qquad (7b)$$

$$Ms = (SP4 - SP3)*(1 + Us) \qquad (8)$$

$$U_{of} - ST1\_3 = \left(\frac{ST2\_3 - ST1\_3}{ST2\_4 - ST1\_4}\right)(U_g - ST1\_4) \qquad (9)$$

$$Ms = (SP4 - SP3)*U_g + U_{of} \qquad (10)$$

The effect of unknown factors on the thin-film thickness is calibrated and compensated for by determining a scaling factor (Us) using Equation (7a) or (7b). The scaling factor (Us) can be determined using only the positive calibration structure 560 or only the negative calibration structure 570. Based on the scaling factor (Us), the effect of molecular interactions, Ms, can be determined using Equation (8). In addition, both the positive and negative calibration structures 560 and 570 respectively can be used to calculate an offset ($U_{of}$) and gain ($U_g$) change of the measurement system caused by unknown factors. This can be accomplished by using a standard two point, (ST1_4, ST1_3) and (ST2_4, ST2_3), linear Equation (9). Based on the calculated U of and Ug, the effect of molecular interactions on the target spot (at the reagent immobilizing sites 530) thickness is determined using Equation (10).

In some implementations, datasets S1 and S2 can be used to monitor the quality of the biochip 500. Contaminations on the surface of the biochip 500 can be determined before reagents are immobilized In implementations where calibration structures (e.g., 140, 592, 596) are not deposited on the transparent thin-film surface (e.g., 512), the height at the normal planar surface 516 (know height of the transparent thin-film layer) can be used to calibrate the height at the target spot 532 (at reagent immobilizing sites 530). In such implementations, Tstep1 and Tstep2 need not be determined. The height at the regent immobilizing sites are determined by normalizing the Tspot measurement (e.g., subtracting Tnorm from Tspot) and comparing the Tspot at different times (e.g., Tspot_1, Tspot_2, Tspot_3 and Tspot_4.)

Because the reagents are immobilized locally (e.g., localized to reagent immobilizing sites 530), thickness measurements at nearby normal surface 516 (without immobilized reagents) can be used as baseline data to compensate for the known system effects or unknown factor effects. The thickness of the measured thin-film layer 512 is usually in the order of one wavelength of the probe light, but both immobilized reagents and target biomolecules interacting with the reagents can cause a change in the local thickness in the order of 1/100 of one wavelength of the probe light. However, for example, the change in thickness due to known system effects and/or unknown factor effects between S3 and S4 measurements may be an increase of 1%. Assuming a 500 nm thick thin-film layer, a 1% change would be and increase from 500 nm to 505 nm. This 5 nm difference is the same order of magnitude change due to molecular interactions, and thus masks the desired change due to molecular interactions. However, since the known system effects are assumed to remain relatively static throughout S1-S4, subtracting the nearby thin-film thickness would allow the 0.05 nm change to be detected.

Biochip Packaging

Figure 8A:
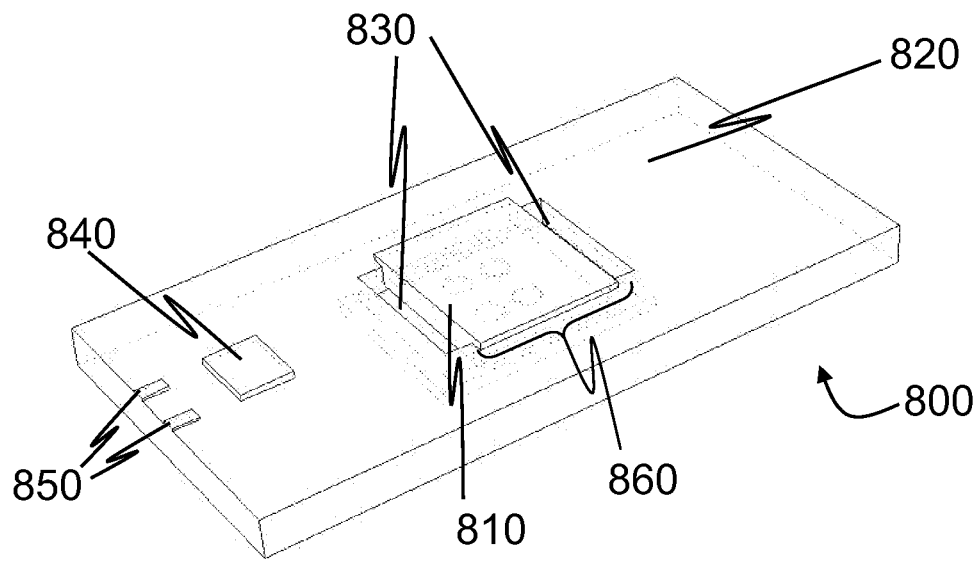
FIGS. 8A and 8B are top-down view of a biochip with optional holder.

FIG. 8A is an angled top-down view of a biochip 800 designed to optimize application of reagents and target biomolecules, in addition to performing thickness measurements. The biochip 800 is substantially as described with respect to FIGS. 1-7. The biochip 800 can be manufactured to physically couple the substrate 810 to an optional holder 820. The substrate is removably attached to the optional holder 820 to securely hold the substrate 810 near or at a fluid injection port 830. The substrate 810 and the optional holder 820 include a physical interface 860 for removable securing the substrate 810. Physical interface 860 can include standard physical interfaces, such as tab-slot, tongue and groove, or other suitable interfaces. The optional holder 820 can further be designed to include a semiconductor memory device 840, a such as a simple EPROM, EEPROM, Flash memory or other semiconductor devices. The optional holder 820 can further include electrical interface connections 850 for providing electrical access to the memory device 840. The memory device 840 is used to store information specific to that particular biochip, e.g., the chip ID, regents in the sample sites 130, and target molecules at sample sites 130, identification of a sample (e.g., patient information) and other information. Data can be written into the memory device 840 by a computer via the interface connections 850. In addition, an optional cover 850 for removably attaching to the optional holder 820 can be included to protect the substrate 810 (see FIG. 8B).

Figure 8B:
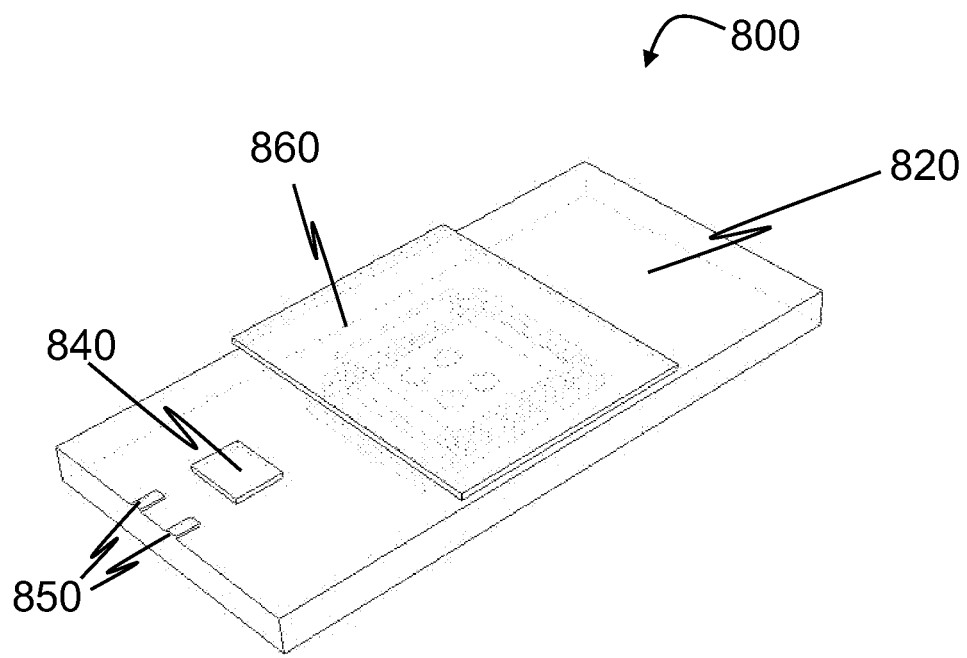
Figure 8C:
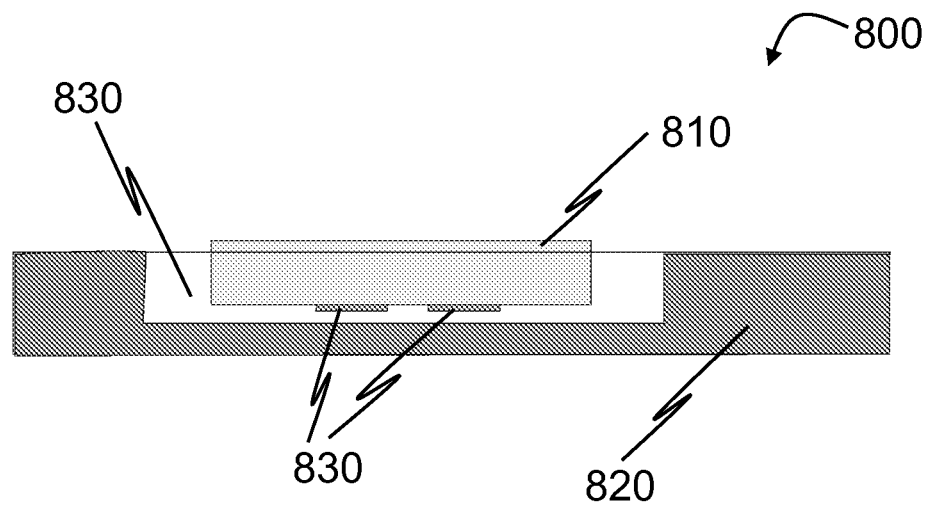
FIG. 8C is a cross sectional view of a biochip with an optional holder.

FIG. 8C is a cross sectional view of the biochip 800 with the substrate 810 removably attached to the optional holder 820. The substrate 810 is removably attached to the optional holder 820 upside-down with the target area (reagent mobilizing sites 830) located on the bottom. In this upside-down configuration, the biochip 800 can be incubated in a solution carrying the target biomolecules for interacting with the immobilized reagents. The solution is injected through injection ports 830. After the incubation period, the substrate 810 can be removed from the optional holder 820 and scanned to detect molecular interactions. In some implementations, the substrate 810 can remain attached to the optional holder 820 and scanned with the reagent immobilizing sites 830 immersed in the solution. A probe beam of light (not shown) can be applied from above the optional holder 820 (entering through the transparent substrate 810) to avoid the air-liquid interface.

In either configurations, when the biochip 800 is scanned and imaged, the height (or thickness or depth) data of the calibration structures (not shown) and the substrate (not shown) (e.g., the transparent thin-film layer on top of the substrate) can be recorded and stored on the on-chip memory device 840. The height data is a 2-D map of the optical substrate height profile, H(ix,iy), where as ix, jy are coordinate indices in x- and y-directions.

In some implementations, a biochip 900 is implemented without an optional holder 920. A sample solution holding the target biomolecules is applied to the optical substrate 910 with reagents immobilized to the reagent immobilizing sites 930. After an incubation process, the sample liquid is washed away, and the biochip 900 is dried before being scanned. In addition, a semiconductor memory device 940 and corresponding electrical interfaces are manufactured directly on the optical substrate 910. In this configuration, the biochip 900 can be implemented in various microarray applications where radioactive or florescent labeled secondary reagents (e.g., antibodies) are used to detect molecular interactions with target biomolecules. In some implementations, secondary reagent molecules are tagged with one or various types of labels including an enzyme (used in enzyme immunoassay (EIA)), radioisotopes such as I-125 used in Radioimmunoassay (RIA) or fluorescent dyes (e.g., Cy3 and Cy5). When the secondary labeled reagent molecules interact (i.e., bind) with the target molecules, a changes in the conformation of the labeled reagent molecules produces an enhancement or quenching of emission (e.g., florescent emission). Some labels, such as florescent dye Cy3 or Cy5 produce emission when excited by a probe of light. Cy3 is excited maximally at 550 nm and emits maximally at 570 nm, in the green part of the spectrum. The quantum yield is 0.15 with FW=766. Cy5 is excited maximally at 649 nm and emits maximally at 670 nm, in the red part of the spectrum. The quantum yield is 0.28 with FW=792.

Implementing a semiconductor memory device 940 on the biochip 900 can benefit various types of microarray chip designs, such as a microarray assay with florescence labeled biomolecules. In such implementations, reagents are immobilized locally, in the form of spots or strips deposited on the top surface of an optical substrate. The substrate can be placed in different solutions where different target molecules can interact with the immobilized reagents on the substrate. One or more molecules in this process is labeled with a florescence dye (e.g., Cy3 or Cy5), and when stimulated with a probe beam of light, emission of different wavelengths of light emission are detected and recorded. Storing the measured data in the on-chip memory device can simplify data management.

The on-chip memory device 940 can include a simple EPROM, EEPROM, Flash memory or other suitable semiconductor devices. In addition, the electrical interface 950 can include one or more electrical contacts compatible with various wired and wireless communication/data transfer protocols. For example, a wired data transfer protocol can include Universal Serial Bus interface and FireWire interface. A wireless data transfer protocol can include Wifi, WiMax, and Bluetooth among others.

Hyperspectrum Imaging System

A biochip 100, 200, 300, 400, 500, 800 or 900 as substantially described with respect to FIGS. 1-9 can be implemented in an imaging system to measure target molecules based on molecular interactions occurring on the reagent immobilization sites (e.g., 130.) FIGS. 10A and 10B are block diagrams of a hyperspectrum imaging system 1000 for scanning and imaging a biochip.1022. The system 1000 includes a computer system 1010, an optical probe 1030 and a X-Y stage 1020. The X-Y stage is designed to hold a target sample (e.g., a biochip 1022) and move the biochip 1022 along X- and Y-axis. The optical probe 1030 includes a light source 1056, one or more optical lenses 1034, 1054, and 1052, a beam splitter 1050, a spectrum analyzer 1040, and an imager 1032. The spectrum analyzer can include an optical grating 1042 and an optical slit 1044. The image 1032 can include a charge-coupled device (CCD) or a semiconductor CMOS image sensor. The computer system 1010 is communicatively coupled to the optical probe for controlling the optical probe and recording spectrum image data captured by the imager 1032.

The system 1000 can be implemented as a hyperspectrum imaging system combined with normal spectrum of color (R,G,B) imaging capability to measure molecular interactions on the optical substrate surface of the sample biochip 1022. The biochip 1022 is substantially as described with respect to FIGS. 1-9 above. Hyperspectrum imaging or mapping provides the entire spectrum at each mapping point of an image to be acquired. Because the entire spectrum is acquired at each image point, a priori knowledge of the sample is not needed, and post-processing allows all available information from the dataset to be mined. Hyperspectrum can be measured either by scanning each point of a target object (e.g., biochip 1022) with spectrometer or by recording series of the images taken at narrow spectral band. Hyperspectrum imaging is described further by Balasi. (See, A Novel Hyper-Spectral Imaging System: Application on in-vivo Detection and Grading of Cervical Precancers and of Pigmented Skin Lesions, by C. Balasi, G. Themelis, In Proc. of "Computer Vision Beyond the Visible Spectrum" CVBVS'01 Workshop, Hawaii, USA, December 2001.)

In hyperspectrum imaging mode, a sample image of the biochip 1022 is projected through the optical slit 1044, and only a narrow band (e.g., a line) of the sample image passes through the optical slit 1044, and projected on the optical grating 1042. The optical slit 1144 is moved onto the optical path and the optical grating is switched to the first optical mode. Moving of the optical slit 1044 and switching the mode of the optical grating 1042 can be performed by an imaging mode controller (not shown) The imaging mode controller can a hardware unit (e.g., a motor, a solenoid, a processor, etc.) and/or a software module controlled by the computing system 1010. In some implementations, the imaging mode controller is an automated function integrated into the hyperspectrum imagines system 1000.

FIG. 10B shows a narrow band 1060 of the sample image being scanned. The narrow band 1060 extends far enough along the Y-axis to scan not only the target spot 1070 (reagent immobilizing site), but also scan calibration structures 1080. The optical grating 1042 is set to operate in the first order optical mode of the grating and disperses the projected image into its constituent wavelengths to produce a full spectrum of the projected image. A lens 1034 focuses the dispersed image on the imager 1032 to be captured (e.g., CCD or CMOS imaging sensor). In the first order mode, the grating is designed to disperse an incident light into its constituent wavelength components. In such implementations, a spectrum of reflected light from a narrow band of the sample image is measured. The X-Y stage 1020 moves the sample (e.g., biochip 1022) through the imager 1032 to measure the spectrum image of the whole sample, one line at a time (i.e., single line scanning).

In some implementations, the optical grating 1042 is switched to operate in the zero order mode to turn off the dispersive function of the grating. In addition the optical grating 1048 is moved out of the optical light path. An incident light simply reflects off the surface of the grating in the zero order mode, and without the optical slit in the image/light path, a normal color (R,G,B) image of the sample (e.g., biochip 1022) is projected onto the imaging sensor. In such implementations, the system 1000 operates in normal imaging mode and alignment features (not shown) or calibration structures deposited on the optical substrate can be used to align the system 1000 before performing spectrum imaging. Such alignment in normal imaging mode enables multiple narrow bands of spectrum imaging data to be aligned correctly.

Since hyperspectrum imaging involves point-by-point or line-by-line scanning, multiple measurements are performed. For example, a biochip 1022 can be scanned up to four times during manufacturing process. These multiple image scans correlated together by using a normal image to help align the sample to a fix initial position. This way, each spectrum image scan can be accurately correlate with other spectrum images. Correlating data in this context includes temporal correlation of the same spatial location image scans.

Figure 9:
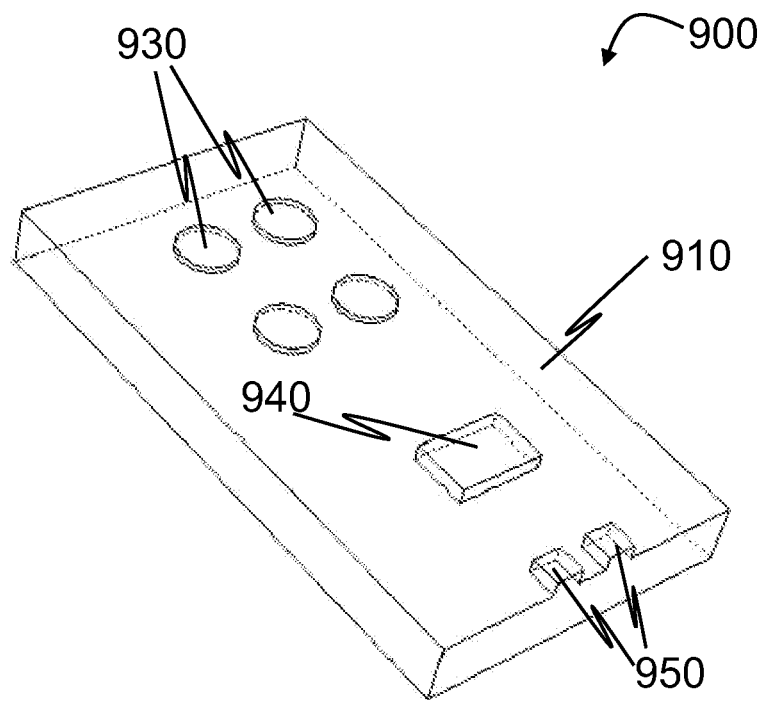
FIG. 9 is a top-down view of a biochip without an alternate holder.
Figure 10A:
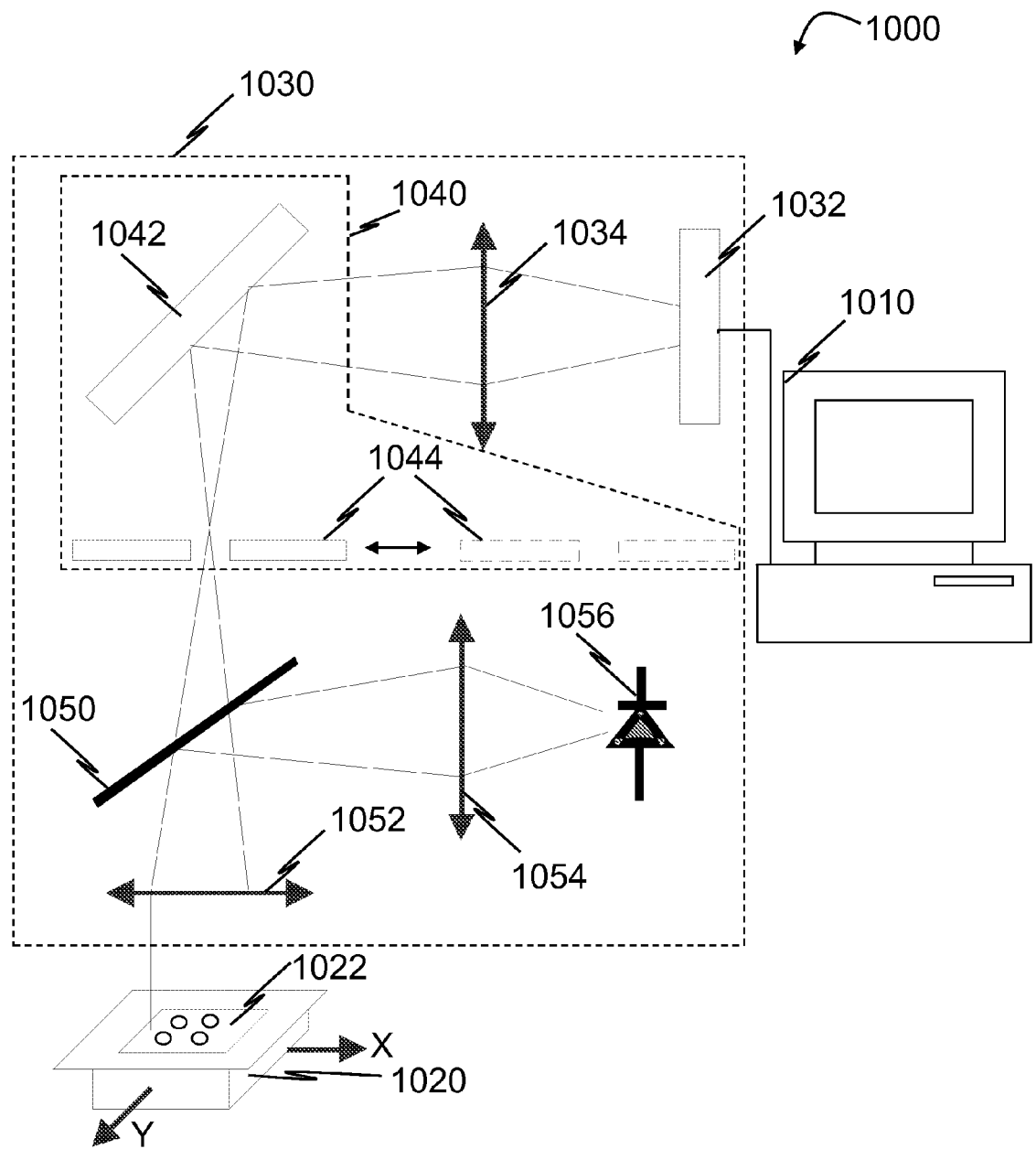
FIGS. 10A and 10B are functional block diagrams of a hyperspectrum imaging system.
Figure 10B:
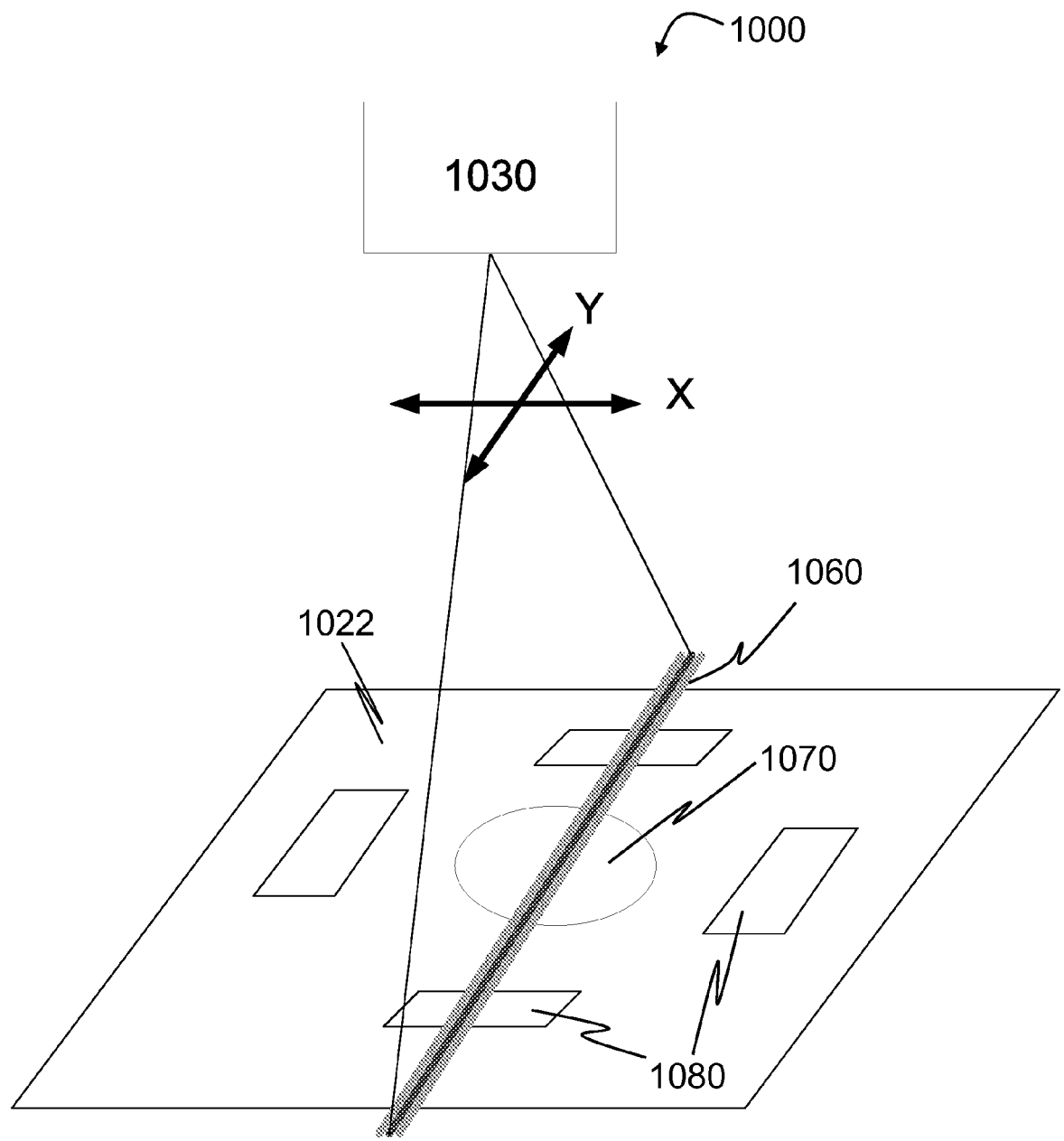

In addition, the biochip 1022 can contain a semiconductor memory device (not shown), as substantially described with respect to FIGS. 8A, 8B and 9, to store each individual scan data locally within the biochip 1022. Such implementations can simplify data management problems, for example, when a biochip 1022 is scanned multiple times by different imaging systems. In addition to measured data, the on-chip memory device can also store manufacturing information, such as quality control information, history of the chip, calibration information, chip design parameters, etc.

In some implementations, a hyperspectrum imaging system can be built on an existing microscopy system. FIGS. 11A-B show a functional block diagram of a hyperspectrum imaging system 1100 designed to be implemented in conjunction with an existing microscopy system 1115. The hyperspectrum imaging system 1100 includes a hyperspectrum module 1130 coupled to an existing microscopy system 1115. The hyperspectrum module 1130 includes a spectrum analyzer 1140, a lens 1134 and an imager 1132. The spectrum analyzer includes an optical grating 1142 and an optical slit 1144. The image 1132 can include a charge-coupled device (CCD) or a semiconductor CMOS image sensor. The computer system 1110 is communicatively coupled to the hyperspectrum imaging system 1100 for controlling the hyperspectrum imaging system 1100 and recording spectrum image data captured by the imager 1132. The hyperspectrum module 1130 is coupled to an existing microscopy system 1115. This coupling can be implemented by attaching the hyperspectrum module 1130 to a microscope camera port 1158 on the existing microscopy system 1115 using standard physical and/or electrical attachments.

The existing microscopy system 1125 includes a light source 1156, one or more optical lenses 1154 and/or 1152 and a beam splitter 1150. The existing microscopy system 1125 also includes a X-Y stage 1120. The X-Y stage is designed to hold a target sample (e.g., a biochip 1122) and move the biochip 1122 along X- and Y-axis. The existing microscopic system 1125 is used to obtain microscopic images of the target sample. The light source can alternatively be implemented using a user design light source (not shown) instead of the built in light source 1156.

The hyperspectrum module 1130 (consisting of spectrum analyzer 1140 and an imager 1132) can be manufactured as a separate unit to add hyperspectrum imaging functions to an existing microscopic system 1115. When used to image a biochip 1122 (designed as described with respect to FIGS. 1-9), a label free and labeled assay can be performed to detect molecular interactions as described with respect to FIGS. 1-10B.

Figure 12:
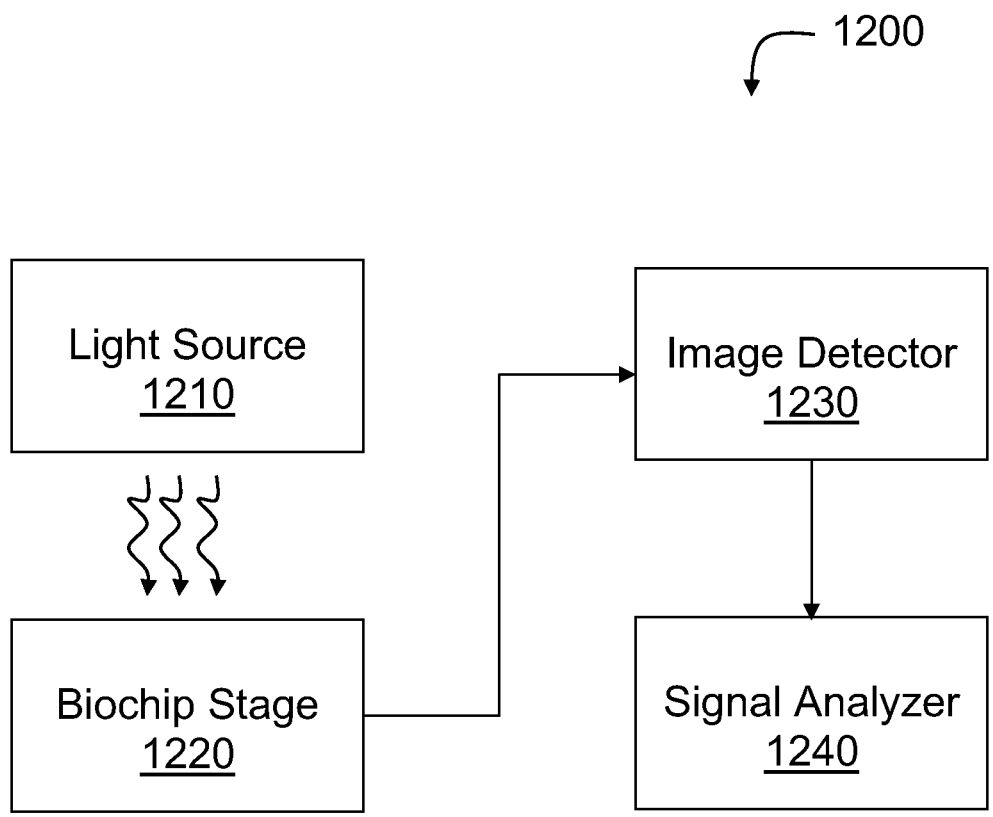
FIG. 12 is a high level view block diagram of a hyperspectrum imaging system.

The hyperspectrum imaging system 1000 and 1100 as described with respect to FIGS. 10A-11B are representative of only some of the variations possible. FIG. 12 is a high level view block diagram of a hyperspectrum imaging system 1200 showing each features in simplified format. In general, a hyperspectrum system 1200 includes a light source 1210, a stage 1220 for holding and moving a sample biochip, an image detector 1230, and a signal analyzer 1240. The light source 1210 can be any visible light source include an LED and fiber optics. The image detector 1230 includes an imaging device, such as a CCD camera and a CMOS camera. The signal analyzer can be any signal and/or data computing device such as a CPU and a computer system.

In some implementations, the hyperspectrum imaging system 1000 and 1100 are used to image and analyze any standard biochip having one or more samples (e.g., an array of samples) for testing. The hyperspectrum imaging system is compatible with a biochip that may not have any or all of the following features: (1) calibration features 140 (see FIG. 1A), (2) alignment markers 145 (see FIG. 1A), (3) memory device 840 (see FIG. 8A), (4) cartridge 820 (see FIG. 8A), and (5) cover 860 (see FIG. 8B). In addition, such standard biochip may include a substrate having various layers composed of various materials. For example, such biochip substrate can include only a single transparent layer.

Labeled & Label Free Assay Applications

A biochip substantially as described in FIGS. 1-10 can be implemented as both a labeled and label-free biochip substrate. The label-free biochip contains reagent immobilizing sites for immobilizing reagents, such as antibodies. Before immobilizing the reagents, an initial measurement provides a baseline image dataset of a blank (no reagents immobilized) biochip. Then, the reagent immobilizing sites on the substrate can be treated with different methods (e.g., surface chemistry) to activate the surfaces of the reagent immobilizing sites for immobilizing reagents. A second measurement can be performed to determine the effect, if any, of the surface activation on substrate thickness. Reagent molecules of choice (e.g., antibodies) are applied to the reagent immobilizing sites to locally immobilize the reagents. A third measurement can be performed to determine the effect of the immobilized reagents on the substrate thickness. After the effect of the immobilized reagents is measured, a sample solution of target biomolecules can be added to the reagent immobilizing sites to detect molecular interactions. For example, conventional Enzyme-Linked ImmunoSorbent Assay (ELISA) techniques or other convention molecular interaction detection techniques (with different label read-out) can be implemented to detect captured molecules. A fourth measurement can be performed to detect molecular interactions based on localized changes in the substrate thickness. The first three measurements can be used to normalize ELISA signals from each image spot, and thus more precise measurements can be accomplished.

Detection of Biomarkers

A biomarker is a substance used as an indicator of a biological state. In biological science and medicine, a biomarker can be a substance whose detection indicates a particular disease state. For example, the presence of an antibody may indicate an infection. Some of the disease pathways include but not limited to Androgen Signaling, Angiogenesis, Apoptosis, Autoimmune and Inflammatory Response, $Ca^{2+}$/NFAT Signaling Pathways, $Ca^{2+}$/NFAT Signaling Pathways, $cAMP/Ca^{2+}$ Signaling Pathway, Cancer Drug Resistance & Metabolism, Cell Cycle, DNA Damage Signaling Pathway, Drug Metabolism, Inflammation & Immunomodulation, Glucocorticoid Signaling, Hypoxia Signaling Pathway, Immunology Signaling Pathways, Insulin Signaling Pathway, JAK/STAT Signaling Pathway, MAP Kinase Signaling Pathway, NFkB Signaling Pathway, Nitric Oxide Signaling Pathway, obesity, p53 Signaling Pathway, PI3K-AKT Signaling Pathway, Signal Transduction in Cancer, Stress & Toxicity Pathway, TGFS Signaling Pathway, Toll-Like Receptor Signaling Pathway, and Tumor Metastasis, Wnt Signaling Pathway.

Biomarkers (e.g., biomolecules, such as proteins) involved in these and other disease pathways can be detected and measured all at once using labeled or label free assay as described above. A biochip and a imaging system as described with respect to FIGS. 1-12 can be implemented to detect the biomarkers using labeled or label free assay. Interactions of biomarkers with the immobilized reagents increases the height or thickness at the reagent immobilizing sites, and the amount of increase in the height or thickness are analyzed to measure the expression levels of the biomarker proteins that are part of the disease pathway of interest. These disease pathways can be built on the biochip (with array of reagent immobilizing sites) based on labeled or label free technology and/or hyper spectrum imaging technology as described with respect to FIGS. 1-12.

Diagnostics Tool

The biomarkers detected using the labeled or label free assays possible through the use of a biochip and/or a hyperspectrum imaging system as described with respect to FIGS. 1-12 can be analyzed to create a diagnostic tool for providing a predictive diagnosis of a specific disease state. The biochip and the hyperspectrum imaging system as described with respect to FIGS. 1-12 can detect multiple biomarkers in a blood sample of a patient. The detected biomarkers can be used with interrelated algorithms to provide a highly predictive diagnosis of selected cancers, cardiovascular disease, metabolic and infectious disease. The capability of the biochip and the hyperspectrum imaging system, as described with respect to FIGS. 1-12, to detect multiple analytes (e.g., proteins) at once allows the detected biomarkers to be analyzed with a disease specific algorithm that provides a highly predictive diagnosis of the corresponding disease. For example, multiple analytes (e.g., multiple protein biomarkers, such as cytokines, chemokines, human growth factors, etc.) involved in a signaling pathways of major depressive disorders can be detected all at once using the biochip and the hyperspectrum imaging system as described with respect to FIGS. 1-12. The detected biomarkers can be analyzed based on a disease specific algorithm to provide a highly predictive diagnosis of one or more depressive disorders.

While this specification contains many specifics, these should not be construed as limitations on the scope of any described technique or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to these variations, other modifications are possible and within the scope of the following claims. For example, in some implementations, in addition to (or instead of) storing the measured data on the on-chip memory device, the data can also be recorded and stored in a storage unit of a computer system (e.g., 1010.) Also, image data can be captured and stored over a computer network.

What is claimed is:
1. An apparatus comprising a biochip, which comprises:
a substrate comprising (1) a transparent layer that at least partially transmits light across a range of wavelengths, (2) a solid dielectric target layer having at least one reagent immobilizing area configured to receive one or more reagents, wherein the target layer is disposed above the transparent layer. and (3) a partially reflective layer disposed between the transparent layer and the target layer, the partially reflective layer having an index of refraction different than the target layer and the transparent layer, and configured to at least partially reflect light across the range of wavelengths, wherein the partially reflective layer and the target layer are arranged such that, when illuminated along a first direction by an incident light beam, a first portion of the incident light beam is reflected from the partially reflective layer and interferes with a second portion of the incident light beam reflected from the reagent immobilizing area to generate an interference signal, wherein an intensity of the interference signal varies in response to a change in light path of the second portion associated with a height of a structure within the reagent immobilizing area; and a calibration structure on the substrate spatially displaced from the reagent immobilizing area and having a predetermined height that is different from a surface of the reagent immobilizing area, wherein the predetermined height of the calibration structure is less than the coherent length of the incident light beam.

2. The apparatus of claim 1, further comprising a cartridge having a support structure for receiving the substrate.

3. The apparatus of claim 2, further comprising a memory device disposed on the cartridge, the memory device configured to store data related to the substrate.

4. The apparatus of claim 1, further comprising a memory device disposed on the substrate, the memory device configured to store data related to the substrate.

5. The apparatus of claim 1, wherein the target layer is composed of a material having an index of refraction different than the transparent layer.

6. The apparatus of claim 1, wherein the target layer is comprises a polymer coating.

7. The apparatus of claim 1, further comprising a polymer layer disposed on the calibration structure, the polymer layer configured to resist absorption of the reagents.

8. The apparatus of claim 1, wherein the calibration structure comprises a positive structure having a predetermined height greater than the surface of the reagent immobilizing area.

9. The apparatus of claim 1, wherein the calibration structure comprises a negative structure having a predetermined height less than the surface of the reagent immobilizing area.

10. The apparatus of claim 1, further comprising a physical barrier disposed on the target layer, the physical barrier having a barrier height greater than the surface of the reagent immobilizing area to prevent movement of reagents beyond the barrier.

11. The apparatus of claim 1, further comprising a reference structure disposed on the target layer of the substrate, the reference structure having a height greater than a coherent length of the incident light beam such that, when the incident is light directed at the reference structure, the incident light beam is reflected off the reference structure and does not interfere with the first portion of the incident light beam reflected from the partially reflective layer or the second portion of the incident light beam reflected from the reagent immobilizing area.

12. The apparatus of claim 1, further comprising a plurality of alignment markers of a predetermined shape, the alignment markers disposed at predetermined locations relative to the reagent immobilizing area on the substrate.

13. The apparatus of claim 1, further comprising a cover removably disposed on the cartridge, the cover configured to protect the substrate.

14. An apparatus comprising a biochip, which comprises:
a substrate comprising: (1) a transparent layer that at least partially transmits light, (2) a sample surface and at least one reagent immobilizing area on the sample surface configured to receive at least one immobilizing reagent that interacts and immobilizes target molecules, wherein the transparent layer is deposited below the sample surface, and (3) a reflective layer disposed between the transparent layer and the sample surface, the reflective layer having an index of refraction different than the sample layer and the transparent layer and configured to at least partially reflect light, wherein the reflective layer and the transparent layer are arranged such that, when the biochip is illuminated along a first direction by an incident light beam, a first portion of the incident light beam is reflected from the reflective layer and interferes with a second portion of the incident light beam reflected from the reagent immobilizing area to generate an interference signal, wherein an intensity of the interference signal varies in response to a change in light path of the second portion associated with a height of a structure within the reagent immobilizing area; and at least one calibration feature formed on the substrate adjacent to the reagent immobilizing area and having a calibration surface above or below the sample surface by a distance that is less than a coherent length of the incident light beam.

15. The apparatus of claim 14, further comprising a cartridge having a support structure for housing the substrate.

16. The apparatus of claim 15, further comprising a memory device deposited on the cartridge, the memory device configured to store data related to the biochip.

17. The apparatus of claim 14, further comprising a memory device deposited on the substrate, the memory device configured to store data related to the biochip.

18. The apparatus of claim 14, wherein the calibration structure comprises a positive structure having a predetermined height greater than the surface of the reagent immobilizing area.

19. The apparatus of claim 14, wherein the calibration structure comprises a negative structure having a predetermined height less than the surface of the reagent immobilizing area.

20. The apparatus of claim 14, further comprising a physical barrier disposed on the sample surface, the physical barrier having a barrier height greater than the surface of the reagent immobilizing area.

21. The apparatus of claim 14, further comprising a reference structure disposed on the sample surface of the substrate, the reference structure having a height greater than a coherent length of the incident light beam such that, when the incident light beam is directed at the reference structure, the incident light beam is reflected off the reference structure and does not interfere with the first portion of the incident light beam reflected from the reflective layer or the second portion of the incident light beam reflected from the reagent immobilizing area.

* * * * *

UNITED STATES PATENT AND TRADEMARK OFFICE
CERTIFICATE OF CORRECTION

| | | |
|---|---|---|
| PATENT NO. | : 8,673,650 B2 | Page 1 of 1 |
| APPLICATION NO. | : 12/305950 | |
| DATED | : March 18, 2014 | |
| INVENTOR(S) | : Bo Pi | |

It is certified that error appears in the above-identified patent and that said Letters Patent is hereby corrected as shown below:

In the Claims:

Column 22, Line 62 (Claim 1), please delete "layer. and" and insert -- layer, and --, therefor.

Column 23, Line 29 (Claim 6), please delete "layer is" and insert -- layer --, therefor.

Column 23, Lines 49-50 (Claim 11), please delete "incident is light" and insert -- incident light beam is --, therefor.

Signed and Sealed this
Tenth Day of June, 2014

Michelle K. Lee
*Deputy Director of the United States Patent and Trademark Office*